United States Patent
Testa et al.

(10) Patent No.: US 9,133,507 B2
(45) Date of Patent: Sep. 15, 2015

(54) APPARATUS AND METHOD FOR PROCESSING BIOLOGICAL SAMPLES AND A RESERVOIR THEREFOR

(71) Applicant: DAKO DENMARK A/S, Glostrup (DK)

(72) Inventors: Gregory A. Testa, Medfield, MA (US); Tim Svenstrup Poulsen, Horsholm (DK); Steen Hauge Matthiesen, Hillerod (DK); Ole Feldballe Rasmussen, Malov (DK); Lars Winther, Smorum (DK)

(73) Assignee: DAKO DENMARK A/S, Glostrup (DK)

( * ) Notice: Subject to any disclaimer, the term of this patent is extended or adjusted under 35 U.S.C. 154(b) by 0 days.

(21) Appl. No.: 14/105,346

(22) Filed: Dec. 13, 2013

(65) Prior Publication Data
US 2014/0099631 A1    Apr. 10, 2014

Related U.S. Application Data

(63) Continuation of application No. 13/472,777, filed on May 16, 2012, now Pat. No. 8,632,739, which is a continuation of application No. 13/016,374, filed on Jan. 28, 2011, now Pat. No. 8,211,385, which is a (Continued)

(51) Int. Cl.
*C12Q 1/68* (2006.01)
*B01L 3/00* (2006.01)
(Continued)

(52) U.S. Cl.
CPC ............... *C12Q 1/6841* (2013.01); *B01L 3/508* (2013.01); *B01L 7/52* (2013.01); *C12M 41/14* (2013.01);
(Continued)

(58) Field of Classification Search
CPC .... C12Q 1/6841; C12M 41/14; C12M 41/36; G01N 1/312; B01L 3/508; B01L 7/52; B01L 2200/142; B01L 2300/1822; B01L 2300/043; B01L 2300/1844; B01L 2300/10; B01L 2300/069; Y10T 436/143333

See application file for complete search history.

(56) References Cited

U.S. PATENT DOCUMENTS

| | | | |
|---|---|---|---|
| 3,825,723 | A | 7/1974 | Roeser |
| 4,654,197 | A | 3/1987 | Lilja et al. |

(Continued)

FOREIGN PATENT DOCUMENTS

| | | |
|---|---|---|
| DE | 19923584 | 1/2002 |
| JP | 10028576 A | 2/1998 |

(Continued)

OTHER PUBLICATIONS

Anonymous, "HybBox™ (for Hybridization)" [online], [retrieved on Aug. 1, 2007], Retrieved from the Internet: <URL: http://www.insitus.com/cathl.html>, Insitus Biotechnologies, Albuquerque, NMUSA.

(Continued)

*Primary Examiner* — Lore Jarrett

(57) ABSTRACT

An apparatus for processing at least one biological sample accommodated on at least one carrier member (15) in a chamber includes, at least one reservoir (18) able to accommodate a fluid on a surface inside the chamber adjacent to and/or facing a substantial part of the at least one biological sample. The apparatus may comprise a bottom member (12) arranged to support at least one carrier member (15) carrying at least one biological sample and a lid (14) including at least one fluid reservoir (18). The reservoir filled with water provides humidity to the chamber and impedes drying out of the sample.

22 Claims, 16 Drawing Sheets

Related U.S. Application Data continuation of application No. 11/031,514, filed on Jan. 7, 2005, now Pat. No. 7,901,634.

(60) Provisional application No. 60/535,615, filed on Jan. 8, 2004.

(51) Int. Cl.
| | | |
|---|---|---|
| *B01L 7/00* | (2006.01) | |
| *G01N 1/31* | (2006.01) | |
| *C12M 1/00* | (2006.01) | |
| *C12M 1/34* | (2006.01) | |

(52) U.S. Cl.
CPC .............. *C12M 41/36* (2013.01); *G01N 1/312* (2013.01); *B01L 2200/142* (2013.01); *B01L 2300/043* (2013.01); *B01L 2300/069* (2013.01); *B01L 2300/0822* (2013.01); *B01L 2300/10* (2013.01); *B01L 2300/1822* (2013.01); *B01L 2300/1844* (2013.01); *Y10T 436/143333* (2015.01)

(56) References Cited

U.S. PATENT DOCUMENTS

| | | | |
|---|---|---|---|
| 4,847,208 | A | 7/1989 | Bogen |
| 4,849,340 | A | 7/1989 | Oberhardt |
| 5,043,143 | A | 8/1991 | Shaw et al. |
| 5,460,780 | A | 10/1995 | Devaney et al. |
| 5,830,413 | A | 11/1998 | Lang et al. |
| 5,908,776 | A | 6/1999 | Burbaum et al. |
| 5,958,341 | A | 9/1999 | Chu |
| 6,117,687 | A | 9/2000 | Hugh |
| 6,225,061 | B1 | 5/2001 | Becker et al. |
| 6,258,593 | B1 | 7/2001 | Schembri et al. |
| 6,358,473 | B1 | 3/2002 | Coello et al. |
| 6,486,947 | B2 | 11/2002 | Modlin et al. |
| 6,534,008 | B1 | 3/2003 | Angros |
| 6,555,361 | B1 | 4/2003 | Lyman et al. |
| 6,673,620 | B1 | 1/2004 | Loeffler et al. |
| 6,703,247 | B1 | 3/2004 | Chu |
| 6,770,441 | B2 | 8/2004 | Dickinson et al. |
| 6,773,676 | B2 | 8/2004 | Schembri |
| 6,790,620 | B2 | 9/2004 | Bass et al. |
| 6,846,454 | B2 | 1/2005 | Peck |
| 7,115,386 | B2 | 10/2006 | Posthuma |
| 7,901,634 | B2 | 3/2011 | Testa et al. |
| 8,211,385 | B2 | 7/2012 | Testa et al. |
| 2002/0001546 | A1 | 1/2002 | Hunter et al. |
| 2002/0001839 | A1 | 1/2002 | Schembri et al. |
| 2002/0006622 | A1 | 1/2002 | Bradley et al. |
| 2002/0192701 | A1 | 12/2002 | Adey |
| 2003/0118482 | A1 | 6/2003 | Peck |
| 2003/0224505 | A1 | 12/2003 | Patno et al. |
| 2004/0029266 | A1 | 2/2004 | Barbera-Guillem |
| 2004/0037739 | A1 | 2/2004 | McNeely et al. |
| 2004/0058437 | A1 | 3/2004 | Rodgers et al. |
| 2004/0110278 | A1 | 6/2004 | Okano et al. |
| 2005/0233409 | A1 | 10/2005 | Posthuma |
| 2007/0269347 | A1 | 11/2007 | Stanchfield et al. |

FOREIGN PATENT DOCUMENTS

| | | |
|---|---|---|
| WO | WO 93/19207 | 9/1993 |
| WO | WO 03/020898 A2 | 3/2003 |
| WO | WO 2004/017376 A2 | 2/2004 |
| WO | WO 2004/025273 A1 | 3/2004 |
| WO | WO 2005/024385 A2 | 3/2005 |

OTHER PUBLICATIONS

Anonymous, Products: Hybridization, Boekel Slide Moad™II [online], [retrieved on Aug. 1, 2007], Retrieved from the Internet: <URL:http://www.boekelsci.com/pages/products/hybridization/pro_hybrid_07.html>, Boekel Scientific, Feasterville, Pennsylvania USA.

Anonymous, The HYBrite System [online], [retrieved on Aug. 1, 2007], Retrieved from the Internet: <URL: http://www.vysis.com1PDF/HYBriteSystem.pdt>, Vysis Inc., Downers Grove Illinois USA.

APPARATUS AND METHOD FOR PROCESSING BIOLOGICAL SAMPLES AND A RESERVOIR THEREFOR

CROSS-REFERENCE TO RELATED APPLICATION

This application is a continuation of application Ser. No. 13/472,777, filed May 16, 2013, which is a continuation of application Ser. No. 13/016,374, filed Jan. 28, 2011, which is a continuation of application Ser. No. 11/031,514, filed Jan. 7, 2005, which claims priority to and the benefit, under 35 U.S.C. 119(e), of the filing date of U.S. Provisional Application 60/535,615, filed Jan. 8, 2004 and titled "Apparatus and Methods for Processing Biological Samples", all of which applications are incorporated by reference in their entirety.

FIELD OF THE INVENTION

This invention pertains to the fields of cytology and histology, molecular biology, biochemistry, immunology, microbiology and cell biology. In particular, the invention is related to the fields of molecular cytogenetics and immunohistochemistry and, even more particularly, to a method and an apparatus for processing, treatment, or even staining of at least one biological sample accommodated on a carrier member, such as a microscopic slide as well as to the control of the humidity and temperature during processing. Applications to which the present invention may relate especially include in-situ hybridization, fluorescent in-situ hybridization, cytology, immunohistochemistry, special staining, and microarrays, as well as potentially other chemical and biological applications.

BACKGROUND OF THE INVENTION

Histological and cytological techniques have been used to analyse biopsies and other tissue samples, as an aid to medical diagnosis and research. Cytology is the study of the structure of all normal and abnormal components of cells and the changes, movements, and transformations of such components. Cells are studied directly in the living state or are killed (fixed) and prepared by for example thin layer preparation systems, embedding, sectioning, and/or staining for investigation in bright field, fluorescent or electron microscopes. Histology is the study of groups of specialised cells called tissues that are found in most multi-cellular plants and animals. Histological investigation includes study of tissue and cell death and regeneration and the reaction of tissue and cells to injury, a disease state such as cancer or invading organisms such as HPV (Human Papilloma Virus). Because normal tissue has a characteristic appearance, histological examination is often utilised to identify diseased tissue.

In situ hybridisation (ISH), and Immunohistochemistry (IHC) analyses are useful tools in histological diagnosis and the study of tissue morphology. In situ hybridisation (ISH), immunocytochemistry and immunohistochemistry (IHC) seek to identify a detectable entity in a sample by using specific binding agents capable of binding to the detectable entity.

A biological sample is in this application to be understood as a biological sample such as histological samples, e.g. tissue and cell specimens, including cell lines, proteins and synthetic peptides, tissues, cell preparations, blood, bodily fluids, blood smears, metaphase spreads, bone marrow, cytology specimens, thin-layer preparations, and specifically biological samples on microscope slides. The biological sample may further suitably be selected from histological material, including formalin fixed and paraffin embedded material, cytological material, fine needle aspirates, cell smears, exfoliative cytological specimens, touch preparations, bone marrow specimens, sputum samples, expectorates, oral swabs, laryngeal swabs, vaginal swabs, bronchial aspirates, bronchial lavage, gastric lavage, blood, urine, and body fluids. Such biological samples may be subjected to various treatments. Further, the biological sample may be suitably selected from non human sources, including virus and fungus swabs, samples taken from medical equipment, veterinary samples and food. Also, samples may be taken from hair, organs, sperm and egg, cells as well as cell grown in vitro. The biological samples are preferably from living or post-mortem tissues of *Homo sapiens*, but not limited to eukaryotic cells. Examples include detection of prokaryotic organisms, such as *Escherichia coli* 0157 in drinking water.

Slides can be any suitable solid or semi solid support for the biological sample. In particular, the support may be a microscope slide, a micro array, a membrane, a filter, a polymer slide, a chamber slide, a dish, or a Petri dish.

The current invention relates especially—but not exclusively—to in situ hybridisation (ISH). In situ hybridisation is a diagnostic method fir characterization and evaluation of genes, chromosomes, cells, cell aggregates, tissues and other biological samples. In situ hybridisation can be used to evaluate and characterize the status, genetic abnormalities and other disease states, such as cancer or disease, caused by infectious organisms. Further, it can be used to characterize cells with respect to infectious agents such as, but not limited to, HPV, HIV (Human immunodeficiency Virus) and HCV (Hepatitis C Virus). Molecular genetic events, such as aneuploidy, gene amplification, gene deletion, RNA expression, RNA transportation, RNA location and chromosome translocations, duplications, insertions, or inversions that are difficult to detect with karyotype analysis, PCR (Polymerase Chain Reaction), or LCR (Ligase Chain Reaction) can be characterized by ISH.

The ISH techniques can have the potential to increase the survival chances of cancer patients by making possible earlier detection of malignancy and more accurate prognostic assessments following tumour surgery. The technique can also be applied to prenatal and postnatal genetic analysis. Furthermore, the technology can be used for simultaneous detection of multiple genetic anomalies in an individual cell, and thereby save assay time and limit specimen requirements.

Non limiting examples of diagnostically important ISH assays include detection of HER-2 (also known as HER-2/neu or c-erbB2), Topo II (breast carcinoma), telomers, EGEr, C-Myc (breast carcinoma), N-Myc (neuroblastoma); translocation probe pairs for BCR/ABL (chronic myelogenous leukemia), EWS (Ewing's sarcoma), C-Myc (Burkitt's lymphoma, T cell ALL), acute myeloid leukemia (AML), myeloproliferative disorders (MPD), Myelodysplastic Syndrome (MDS) and centromeric probes for chromosomes 17, 7, 8, 9, 18, X, and Y. Other examples include the analysis of Epstein-Barr virus, Herpes simplex virus and Human cytomegalo virus, Human papilloma virus, Varizella zoster virus and Kappa and Lambda light chain mRNAs. Yet other examples include the detection and analysis of samples of non-human origin, for example, food borne parasites and disease causing microbes and viruses. More specific examples include:

i) the analysis of HER-2/neu, also known as c-erbB2 or HER-2, which is a gene that has been shown to play a role in the regulation of cell growth. The gene codes for a transmembrane cell surface receptor that is a member of the tyrosine kinase family. HER-2 has been shown to be amplified in human breast, ovarian and other cancers;

ii) the analysis of aneuploidy for chromosomes 3, 7, 17 and loss of the 9p21 locus in urine specimens from patients with transitional cell carcinoma of the bladder;

iii) the detection and quantification of the lipoprotein lipase (LPL) gene located at 8p22 and the C-MYC gene located at the 8q24 region (Two genetic alterations observed in abnormal cells, such as Prostate cancer samples, are gain of 8q24 and 8p21-22 (LPL) loss of heterozygosity.);

iv) the identification and enumeration of chromosome 8 in cells obtained from bone marrow. An association has been made between trisomy 8 and both myeloid blast crisis and basophilia (Trisomy 8 is a prevalent genetic aberration in several specific diseases like Chronic Myelogenous Leukemia (CML), acute myeloid leukemia (AML) and myeloproliferative disorders (MPD).);

v) the analysis of chromosome aneuploidy like translocations of the immunoglobulin heavy chain locus (IGH) located at 14q32 and frequently observed in patients with various hematological disorders (These IGH translocations result in the upregulation of oncogenes due to the juxtaposition of IGH enhancers with these oncogenes.);

vi) the identification of inv(16)(p13q22) where the CHFB gene located in 16q22 is fused to the MYH11 gene located in 16p13, resulting in a chimeric protein product detected in acute myeloid leukemia (AML);

vii) the detection of Human Papilloma Viruses (HPV), which are a group of small DNA viruses (There are more than 90 HPV types. Persistent HPV infection may result in cervical cancer, and has also been associated with other types of cancer, e.g. colon cancer. HPV types are classified according to the risk associated with the development, of cervical cancer. Fifteen types are classified as high-risk, and these are detected in more than 99% of all cervical cancers.).

In summary, the in situ Hybridization (ISH) technique is a useful method for the analysis of cells for the occurrence of chromosomes, chromosome fragments, genes and chromosome aberrations like translocations, deletions, amplifications, insertions or inversions associated with a normal condition or a disease. Further, ISH is useful for detection of infectious agents as well as change in levels of expression of RNA.

The ISH techniques should be understood to include, for example, fluorescent in situ hybridization (FISH), chromogenic in situ hybridization (CISH), Fiber FISH, CGH, chromosome paints and arrays. In the following, the ISH technique and procedures are described in greater detail. ISH uses nucleic acid probes, designed to bind, or "hybridize," with the target DNA or RNA of a specimen, usually fixed or adhered to a glass slide. DNA, RNA, PNA, LNA or other nucleic acid probes of synthetic or natural origin can be used for the ISH technique. The probes are labelled to make identification of the probe-target hybrid possible by use of a fluorescence or bright field microscope. The probe is typically a double or single stranded nucleic acid, such as a DNA or RNA. It is labelled using radioactive labels such as 31P, 33P or 32S, or non-radioactively, using labels such as digoxigenin, or fluorescent labels, a great many of which are known in the art. The hybrid is often further analysed with computer imaging equipment. Since hybridization occurs between two complementary strands of DNA, or DNA analogues, labelled probes can be used to detect genetic abnormalities, providing valuable information about prenatal disorders, cancer, and other genetic or infectious diseases.

Unlike other molecular DNA-based tests, which require cell lysis to free nucleic acids for analysis, ISH allows analysis of DNA in situ, that is, in its native, chromosomal form within the cell or even the nucleus. This feature permits the analysis of chromosomes, genes and other DNA/RNA molecules of individual cells. For direct-labelled, probes, the results are detected by viewing the samples under a fluorescence microscope with appropriate filters. Indirect detection, like CISH, demands additional labelling steps, which typically require streptavidin or antibody-enzyme conjugates or fluorophore-labeled counterparts, and additional washing steps once the probe is bound to the target.

An exemplified general ISH procedure includes one or several of the following sequential procedural steps:
  i) Mounting of the biological sample on slides
  ii) Baking at elevated temperatures
  iii) Dewaxing or deparaffination if necessary
  iv) Washing
  v) Target retrieval at elevated temperature
  vi) Denaturing at elevated temperature
  vii) Incubation with blocking reagents
  viii) Addition of probe mixture to the sample on the slide.
  ix) Placing, a coverslip over the sample and the probe mix and sealing with rubber cement.
  x) Hybridization at elevated temperatures.
  xi) Washing at elevated temperatures and removal of coverslip
  xii) Air drying and counterstaining
  xiii) Visualization according to the instruction for FISH or CISH
  xiv) Examination and evaluation in a microscope In more detail, an exemplified FISH protocol for paraffin embedded tissue sections could include one or several of the following sequential procedural steps:
  i) Cutting 2-4 micrometer tumour sections from a block
  ii) Mounting on slides
  iii) Baking at 60° C. for 30 minutes
  iv) Deparaffination using xylene
  v) Rehydration by immersing in ethanol/water mixtures
  vi) Pre treating by washing with an aqueous buffer for 10 minutes at 95° C.
  vii) Pepsin digesting for 10 minutes at ambient temperature
  viii) Washing repeatedly
  ix) Dehydration in a series of cold ethanol/water mixtures
  x) Air drying
  xi) Addition of 10 microliter fluorescent labelled DNA or PNA probe mixture per slide
  xii) Sealing with a 22 by 22 mm glass coverslip and rubber cement at the edges
  xiii) Denaturing at 82° C. for 5 minutes, directly followed by
  xiv) Hybridization over night (18 hours) at 45° C.
  xv) Removal of the coverslip
  xvi) Stringent washing at 65° C. for 10 minutes
  xvii) Washing repeatedly with wash baler
  xviii) Dehydration by immersing in a series of cold ethanol/water mixtures
  xix) Air drying
  xx) Mounting with 10 microliter anti fade solution with DAPI as counter stain
  xxi) Sealing with a coverslide
  xxii) Examination and evaluation in a fluorescence microscope The hybridization mixture is typically a complex mixture of many components. Non-limiting examples of components include formamide, water, triton x-100, tween 20, Tris or Phosphate buffer, EDTA, EGTA, polyvinylpyrolidine, dextran sulfate, Ficoll, or salmon sperm DNA.

Chromogenic in situ hybridization (CISH) uses labelled probes, which can be visualized by the use of immunological staining methods similar to the IHC staining procedures. CISH has some differences compared to FISH techniques: The genetic aberrations may be viewed within the context of tissue morphology—simultaneous examination of histopathology and ISH results. Also, the results may be visualized, with a standard bright field microscope, and the chromogenic dye (for example DAB) generated on the slide is permanent with no or little fading of fluorescent signals.

In addition to ISH, the current invention also relates to immunohistochemistry and immunocytochemistry. The general exemplified formalin fixed paraffin embedded (FFPE) immunohisto chemical (IHC) chromogenic staining procedure may involve the steps of: cutting and trimming tissue, fixation, dehydration, paraffin infiltration, cutting in thin sections, mounting onto glass slides, baking, deparaffination, rehydration, antigen retrieval, blocking steps, applying primary antibody, washing, applying secondary antibody-enzyme conjugate, washing, applying enzyme chromogen substrate, washing, counter staining, cover slipping and microscope examination.

As described above, the sample treatment of the slides is complicated, laborious and uses many different reagents at various temperatures for prolonged periods. It should be understood that under normal conditions only small amount of reagents, 200 µl or even less, are applied to the sample. Thus, the reagent and sample are very easily dried out, especially under high temperatures and at low relative humidity. Many of the procedural steps in BR including the denaturing and the hybridization steps are typically done in a humidity chamber. The humidity chamber is a closed or semi closed container in which the slides can be processed and heated. It should be understood that the processing temperature as well as the temperature ramp time—that is, the change of temperature per time unit, is important for both the overall protocol length and the subsequent visualized result. Furthermore, it has been observed that the staining result depends strongly on the humidity during the sample treatment. Also, the morphology can suffer from drying out during the treatment. For example, chromosome spreads are easily ruined due to drying out conditions. During the changes of temperatures the air above the slides will expand or contract. The reduction in pressure during lowering of the temperature will draw in air from the outside, which may be less saturated with water compared to the air above the slide. During heating, air will be pressed out of the space between the slide and the lid. This air will contain moisture, which will escape from the system. Consequently, due to the plurality of fast and repeated changes in temperature, high temperatures for prolonged time and the small space between the slides and the lid, moisture can escape either quickly, or over time, from the system, resulting in a change in the concentration of the reagents applied to the biological sample and thus a change in the protocol, or even drying out of the biological sample.

The absolute humidity is defined as the amount of water in a given volume of gas. The relative humidity is the ratio between the amount of water and the maximum amount of water possible at the given temperature and pressure. The maximum amount of water per volume, and consequently the relative humidity, depends strongly on the temperature, as described by the Clausius-Clapeyron equation. For example, without addition of water in a closed system, 100% relative humidity at 25° C. will correspond to 16.3% at 60° C. and 3.7% at 95° C., indicating the strong dependence of temperature. Even a small change of temperature will change the relative humidity dramatically. For example, a relative humidity of 100% at 80° C. will correspond to only 66.7% at 90° C. in a closed system without addition of moisture.

From the discussion above, it should be clear that precise control of humidity, heating and cooling is essential for obtaining, for example, consistent ISH results. Therefore, without an efficient humidifying system, heating of the slides can result in fast drying out of the reagents or sample.

DESCRIPTION OF PRIOR ART

In order to prevent drying out or loss of "reagents" of the slides, several different closed humidifying systems are known to be used in the cytogenetic, pathology and research laboratories during for example the critical steps of denaturation and hybridization.

U.S. Pat. No. 6,555,361 discloses a hybridization chamber that contains a built-in mechanism for saturating the air within the chamber when sealed thereby preventing drying of the liquid sample. The hybridization chamber is defined by matching top and bottom clam-shell like halves that, when brought together, are sealed by an o-ring and clamping device. The chamber is equipped with a liquid reservoir, the liquid from which will serve to saturate the volume of air sealed within the hybridization chamber. A saturated atmosphere within the chamber prevents evaporation of the sample. This patent illustrates an interior chamber sized to receive a glass microscope slide and suggests positioning a well within the chamber to retain liquid separately from the region for holding a liquid sample. Further, it is suggested to dispose a microporous membrane material in the chamber and specifically in the well. The control of temperature and humidity inside the chamber during rapid warm-up or cool-down periods is not discussed in this patent document.

Humid boxes or humidified chambers are typically plastic containers with a lid. Water-soaked paper towels are placed in the bottom of the box and excess water decanted away. Slides in racks can be placed horizontally or vertically in the box during for example overnight hybridization. Typical "home-made" humid box laboratory equipment includes standard Tupperware™ or Rubbermaid™ boxes or standard cake pans with a tight closing lid. Wet paper tissue is placed in the bottom. A frame or grid is placed over the tissues and the slides placed on the frame or grid before the lid is closed. The humid box is placed in a conventional or microwave oven or on top of a heating plate during for example the denaturation or hybridization steps. To further control the humidity and temperature profile, the humid box can be isolated to limit heat loss and thereby hold the temperature for longer periods.

An insulated box like e.g. the HybBox™ (InSitus BioTechnologies, Albuquerque, N. Mex., USA) made of expanded polystyrene with a base and a lid is an attempt to further control the humidity and temperature during for example hybridization. After denaturation of the biological sample on slides in an oven, the slides are transferred to the HybBox™, which is tightly closed. After hybridization, the box is opened and the slides further treated.

To further control the temperature profile during general slide processing, several temperature-controlled chambers are commercially available. One example is the Boekel Slide Moat™ (Boekel Scientific, Feasterville, Pa., USA) consisting of a temperature controlled heating block. Up to 30 standard microscope slides can be placed horizontally on the heating block. A glass lid with seals closes over the heating block and the slides. Placing wet towels on the heating block together with the slides can give high humidity.

The HYBrite™ Denaturation/Hybridization System (Vysis, Abbott Laboratories, Downers Grove, Ill., USA) is another temperature controlled humid chamber widely used in, especially, ISH laboratories. It consists of a programmable heating plate on which up to 12 microscope slides can be placed. A lid comes down over the heating plate and slides and closes the system. On each side of the slide heating plate, wells or channels can hold water or wet tissues or towels. Humidity is thereby sought controlled by the use of wet tissues or towels. Once the slides are placed in the instrument and the lid is closed, sequential denaturation and hybridization steps can be performed automatically without the intervention of the user.

In an attempt to further control the temperature and avoid small temperature fluctuations, the TruTemp heating system (Matrix, Hudson, N.H., USA) uses a heated lid in addition to the heated slide block. The instrument consists of a programmable heating, block on which the slides are placed. The lid is further heated. Humidification is provided by water added to wells integrated into the heating block on which the slides rest.

Typically, the user can program the various commercially available temperature controlled humid systems with many time-temperature protocols from 0 to more than 24 hours and from ambient temperature to 100° C.

In yet another attempt to automate the temperature and humidity during processing, automated instruments using so called liquid coverslip systems (Ventana Medical Systems, Tucson, Ariz.) have been introduced. The limiting of drying out of slide-mounted specimens has been sought by covering the reagents and sample with an immiscible oil. The system only limits the evaporation, resulting in loss of a significant part of the reagent volume and is not practical for hybridization in more than 12 hours at elevated temperatures.

The instruments eliminate a number of steps and reduce hands-on time required during conventional ISH procedures performed by cytogenetic, pathology and research laboratories. Nonetheless, the manual systems using ovens and various plastic containers, in general, still give the best results with regard to both preserved morphology and staining efficiency. The semi or fully automated humid boxes or chambers have the advantage of e.g. less hands-on work and ease of use. However, none of the semi or fully automatic humid boxes or chambers has succeeded in providing a performance equivalent to or exceeding the manual methods, with respect to preserved morphology and staining efficiency. The humidity control is closely connected to the temperature, as discussed previously, but is not easily controlled. Also, no known system has truly addressed the problem of having both controllable uniform temperature and uniform and high humidity over the slides for prolonged time.

In light of the above discussion, there is a need in the art for an improved treatment device for treating biological samples. In summary, the improved sample treatment device should ideally include: programmable temperature control; precise control of heating and cooling; fast change of temperature; independence of the number of slides treated; high humidity at any relevant temperature; constant humidity for prolonged periods; and uniform temperature and humidity over the slides. The present invention addresses such a need.

SUMMARY OF THE INVENTION

The present invention provides an apparatus for processing biological samples, the apparatus comprising means for processing at least one biological sample accommodated on at least one carrier member, characterised in that at least one reservoir able to accommodate a fluid is arranged on a surface adjacent to and/or facing a substantial part of the at least one biological sample. The proximity of the fluid reservoir and the sample is important in order to ensure that vapor from the reservoir can be generated at a rate able to maintain a constant high relative humidity in the chamber formed around the sample by the inner surfaces of the apparatus during a heating period with raising temperature.

In a preferred embodiment, the reservoir is arranged above the at least one sample on the at least one carrier member.

In a preferred embodiment, the apparatus comprises a bottom member arranged to support at least one carrier member carrying at least one biological sample and characterised by further comprising a lid including at least one fluid reservoir. The preferred position of the fluid reservoir is on the lower surface of the lid. This ensures the optimal proximity to the samples.

In a preferred embodiment, the lid member is provided with holding means, such as a grid, slots and/or fingers (not shown), supporting the at least one fluid reservoir, arranged to be located above the biological samples when the lid is closed, thereby covering the bottom member.

In a preferred embodiment, an apparatus according to the invention is characterized in that the reservoir is placed less than 5 cm from the carrier member, and, preferably, less than 1.0 cm from the carrier member, and, yet more preferably, less than 0.50 cm from the carrier member.

10080 Preferably, an apparatus according to the invention is characterized in that the macroscopic surface area of the reservoir adjacent to and/or facing the sample on the carrier member is more than 10% of the total carrier member area, and, preferably, more than 30% of the total carrier member area and, even more preferably, more than 60%. The extension of the reservoir plays an important role in the same way as the proximity by improving the rate by which the relative humidity may be dinged as well as the ability to maintain a prescribed high relative humidity during a rapid heating period with raising temperature.

Preferably, an apparatus according to the invention is characterized by comprising heating means for heating the sample on the carrier member. Preferably, the heating means are incorporated in the apparatus.

Preferably, the apparatus is characterized by comprising temperature controlling means controlling the temperature of the carrier member and thereby, the temperature of the biological sample on the carrier member. Preferably, the apparatus includes temperature controlling means enabling an automatic heating of the sample according to instructions prescribed in a protocol defining the desired processing of the sample.

Preferably, the apparatus is characterized by comprising at least one temperature sensor connected to the temperature controlling means.

In a preferred embodiment the heating means are heating wires. Alternatively, the heating means may be inductive heating.

Preferably, the temperature controlling means comprises cooling means for cooling the sample on the carrier member. The prescribed processing of a biological sample typically involves cooling after a period of heating. In a preferred embodiment the cooling means are Peltier elements and/or at least one fan.

In a preferred embodiment, the apparatus may comprise heating means for heating the reservoir, and the temperature controlling means may enable control of humidity in the chamber by changing the temperature of the reservoir and/or sample by activating the heating means or the cooling means in the bottom member of the apparatus and/or in the lid.

In a preferred embodiment of the apparatus, the heating means for heating the sample on the carrier member and the heating means for heating the reservoir are controlled separately, and may be heated to different temperatures, so that the reservoir may become warmer than the sample or vice versa. In this manner, the control of the relative humidity within the chamber around the sample may be highly improved as a high humidity may be generated fast by raising the temperature of the reservoir, thereby releasing vapor molecules into the atmosphere in the chamber and thereby around the sample. Dependent on the temperature of the sample and the reagents on the sample and such temperature can be controlled by heating or cooling the support of the sample the vapor may stay in a balance with the reagents and the sample or may concentrate on the sample and in the solution comprising the reagents, Alternatively, if a lower humidity is desired, this may be obtained by lowering the temperature of the reservoir so vapor tends to concentrate on the reservoir and become absorbed by the reservoir so vapor can be extracted from the atmosphere around the sample in case a drying out oldie sample should be desired.

It is an essential advantage of the new apparatus according to the invention that a complete control of temperature and humidity in the atmosphere around the biological sample is made possible.

In a preferred embodiment of the apparatus, the reservoir is shaped as a substantially flat sheet. Preferably, the thickness of the reservoir is less than 1/10 of the length, so that the external surface—also called the macroscopic surface—is large compared to the volume. It is essential that the reservoir can contain a sufficient volume of water, but it is even more essential that the surface enabling an exchange of vapor in and out of the reservoir is large enough to enable a rapid release or absorption of vapor.

In a preferred embodiment of the apparatus, the reservoir is attached to a lid, which, in a closed position, covers the at least one biological sample on the carrier member lying on a temperature-controlled plate. In another preferred embodiment of the apparatus, the reservoir is the lid, which, in a closed position, covers individual slides with individual temperature controlled plates. In yet another preferred embodiment of the apparatus, the reservoir is the lid, which, in a closed position covers several slides lying on a number or temperature-controlled plates.

Preferably, in the apparatus according to the invention, the reservoir may have a curved surface structure and uneven surfaces, such as a corrugated surface.

Preferably, the fluid in the reservoir is a liquid and the reservoir comprises a medium able to adsorb and/or absorb and desert) and/or release the liquid. Preferably, the fluid is substantially pure water. Alternatively, the fluid may be water including additives, such as an anti-microbial agent, The fluid may comprise formamide, aqueous buffers, alcohols, dimethylformamide, dimethylsulfoxide, N-methyl-pyrolidone, non-aqueous buffers or complex mixtures containing inorganic salts, detergents, pH buffers, organic solvents, glycerol, oil and/or water, or mixtures thereof.

Preferably, the reservoir is a device made of a material having a very high internal surface area, such as artificial and natural sponges, comprising a plurality of cavities able to accommodate a fluid. Preferably at least a substantial portion of the surface(s) is hydrophilic.

Preferably, the reservoir is made of a material from the group comprising polymeric fiber composites and blends, glass fiber materials, expanded porous polymers, porous ceramics, Rockwool™, wood pulp, cardboard, leather or celluloses based materials.

Preferably, the reservoir is made of a material comprising any of the compositions from the group comprising polyethylene, polypropylene, polyurethanes, polysulfones, polyvinyl, polyamide, polyisobutylene, siloxane polymers, polyacrylic compositions, ethylene Vinyl Acetate, viscose rayon, polystyrene, macroreticular polystyrene, aliphatic, or phenol-formaldehyde condensate polymers, epoxy, cotton, polysaccharide, modified polysaccharides, wood pulp, calcium carbonate, silica gels, glass fiber, bentonite, perlite and zeolite.

Preferably, the reservoir is made of a material from the group comprising manmade or synthetic polymeric bonded, non-bonded, woven or knitted fibers, micro fibers, textiles and tufted textiles. Preferably, the reservoir is made of a material from the group comprising bonded polyamide, polyester, polyolefines Mid cellulose acetate fibers. Preferably, the material is made of non-woven and bonded blends of hydrophilic modified polypropylene and polyethylene micro fibers. Preferably, the material is made of bundles of fibers or other loose material retained by a thin wall of film.

Preferably, the reservoir material has a density from 0.050 to 1.5 gram/cm$^3$ and, more preferably, from 0.075 to 0.75 gram/cm$^3$. Preferably, the reservoir material has the ability to hold at least a predefined minimum volume of liquid per carrier member. Preferably, the reservoir material has the ability to hold at least 10 micro-liters ($\mu$l) in total per carrier member, and, more preferably, more than 100 micro-liters ($\mu$l) in total per carrier member, such as more than 200 micro-liters ($\mu$l) in total per carrier member, and even more than 500 micro-liters ($\mu$l) in total per carrier member, and such as more than 1000 micro-liters ($\mu$l) in total per carrier member.

Preferably, a further reservoir is arranged on top of the lid for fluid communication with the absorbing and desorbing reservoir opposite to the biological sample. The further reservoir can easily be refilled with water without opening the hybridising chamber, and the further reservoir may be in fluid communication with the reservoir material though thin channels in the lid allowing the water to ooze or flow slowly towards the reservoir material.

The current invention has solved the problem of control of humidity from an ISH or IHC reaction by having a liquid reservoir very close to and adjacent to, preferably facing, the sample on the slide. Furthermore, the reservoir is designed for fast exchange of humidity between the liquid phase in the reservoir and the vapor phase in the space between the slide and the lid.

The invention also relates to a reservoir. The reservoir according to the invention is characterised in that the reservoir comprises a medium capable of adsorbing and/or absorbing and desorbing and/or releasing the liquid.

Preferably, the reservoir may be shaped as a substantially flat sheet or plate, so that the surface of the reservoir facing the sample is large, preferably larger than the surface of the sample. Preferably, the thickness of the reservoir is less than 1/10 of the length, in order to fit into the chamber surrounding the at least one sample. Typically, the sample support and the cover or lid forming the chamber around the sample can be designed to leave only a little free space between the sample and the cover or lid. By minimising the volume of the chamber, it is easier to limit the evaporation from the sample as well as to control the content of the atmosphere in the small chamber.

In one embodiment, the reservoir may have a curved surface structure and uneven surfaces, such as a corrugated surface, in order to increase the surface area.

Preferably, the macroscopic surface area (external surface area) of the reservoir adjacent to and/or facing the sample on the carrier member is more than 10% of the total carrier member area, and, more preferably, more than 30% of the total carrier member area and, even more preferably, more than 60%.

Preferably, the reservoir is a device made of a material having a very high internal surface area, e.g. comprising a plurality of cavities able to accommodate a fluid, or wherein the material is made of bundles of fibers or other loose material retained by a thin wall of film. Preferably, at least a substantial portion of the surface(s) is hydrophilic.

Preferably, the reservoir may be impregnated with an anti microbial agent or other protective agents. Preferably, the type, shape and size of the reservoir material are selected to optimise surface properties to match with the liquid surface tension.

The reservoir is a device that can contain liquids, e.g. water, located above or adjacent to the slides and the heating plate below the slides. The liquid can be contained in the reservoir over the slides despite the gravitational forces.

The reservoir has the ability to fast adsorb and/or absorb as well as desorb and/or release liquids. The reservoir is preferably made of a material with very high surface area, The reservoir can be made of a number of different materials, non-limiting examples including polymeric fiber composites and blends, glass fiber materials, expanded porous polymers, porous ceramics, Rockwool™, wood pulp, cardboard, leather or celluloses based materials.

Further non-limiting examples of reservoir materials include materials containing polyethylene, polypropylene, polyurethanes, polysulfones, polyvinyl, polyacrylic, ethylene Vinyl Acetate, viscose rayon, polystyrene, macroreticular polystyrene, aliphatic, or phenol-formaldehyde condensate polymers, epoxy, cotton, polysaccharide, modified polysaccharides, wood pulp, calcium carbonate, silica gels, glass fiber, bentonite, perlite or zeolite. Even a grid of thin steel wires may provide a reservoir for a liquid.

Preferable materials include manmade or synthetic polymeric bonded, non-bonded, woven or knitted fibers, micro fibers, textiles or tufted textiles. More preferably, the materials are made of bonded polyamide, polyester, polyolefines or cellulose acetate fibers. Even more preferably, the material is made of non-woven and bonded blends of hydrophilic modified polypropylene and polyethylene micro fibers. Further, it should be understood that the reservoir material could be made of bundles of fibers or other loose material retained by a thin wall of film.

The material can be selected to optimise surface energy to match with the liquid surface tension. The surface properties of the material can be due to the hulk material or from specific chemical, plasma or irradiation surface treatments. Such treatments are well known to the person skilled in the art of polymer chemistry.

The high internal surface areas can adsorb and later desorb a wide variety of different liquids depending on the environment in which they are used. The relative humidity over the sample on the slide is a consequence of the absorption characteristics of the reservoir material and the temperature. Because of the variation options, such as the type, surface properties, shape and size of the reservoir material, the porosity, and the pore size, the broad spectrum of requirements of humidification action can be fulfilled.

The reservoir should be selected from materials having a density from 0.050 to 1.5 gram/cm$^3$, and, preferably, from materials having a density from 0.075 to 0.75 gram/cm$^3$. Experience has proven that such density of the preferred porous or fibrous materials provides the desired absorbing and desorbing features.

The reservoir should be selected from materials and geometrical shapes having the ability to hold at least a predefined minimum volume of liquid per carrier member or microscope slide. Preferably, the reservoir has the ability to hold at least 10 microliters in total per carrier member, and, more preferably, more than 100 microliters in total per carrier member, and, yet more preferably, more than 200 microliters in total per carrier member, and, even more preferably, more than 500 microliters in total per carrier member, and, most preferably, more than 1000 microliters in total per carrier member.

The ability to hold the water is essential, as any water drops on the sample would deteriorate the staining of the sample. Also, a high amount of water in the reservoir is important to obtain a high rate of exchange of humid air in order to maintain the desired humidity above and within the sample.

Preferably, the reservoirs are in the form of flat sheets or plates. Preferably, they may have a curved surface structure and uneven surfaces such as a corrugated surface to optimise the surface area.

Preferably, the reservoir is sufficiently rigid and stable and self-supporting, and does not creep or bend downward. Also preferably, the reservoir does not markedly swell or change shape during desorption or adsorption of liquids or due to change in temperature.

Preferably, the reservoir is placed less than 5 cm over the slides. More preferably, the reservoir is placed less than 1.0 cm over the slides, and, yet more preferably, less than 0.50 cm over the slides.

It should be understood that the slides and reservoir could be in a tilted or vertical or horizontal position. It is the position of the reservoir adjacent to or facing the sample on the slide which is essential. Also, the arrangement of slides and reservoir could be turned upside down, so that the reservoir will be located below the slide.

The macroscopic surface area (the external surface) of the reservoirs facing towards the slides should preferably be more than 10% of the total slide area. More preferably, the area should be more than 30% of the total slide area. Even more preferably, the area should be more than 100% of the total slide area. The macroscopic surface area of the reservoirs should be understood as the external area of the reservoirs and not the internal surface area of the fibers or cavities.

In one preferred embodiment, the reservoir is attached to a lid, which comes down over the slides lying on a temperature-controlled plate. Thereby, the slides are enclosed in a closed controllable space, preferably provided with temperature sensors controlling the climate. In another embodiment, the reservoir is placed between slides and the lid, which comes down over the slides lying on a temperature-controlled plate. In yet another embodiment, the reservoir is the lid, which comes down over individual slides with individually temperature-controlled plates, or several slides lying on a temperature controlled plate or plates.

It should be understood that the cover or lid could cover one, two or several slides on the temperature-controlled plate or the individually temperature-controlled plates.

In yet further embodiments, the reservoir as described above may be further temperature controlled by a heating device above the reservoir. Preferably, one or more sensors are arranged for sensing temperature above the slide(s).

If the reservoirs are attached to the lid and are to be changed, it is preferred to have small handles or perforated taps in the material for easy manual manipulation.

Preferably, heating from beneath the slide controls the temperature of the slide and biological sample. However, it should be understood that the reservoir could also be heated. Preferably, this can be done by electrical heating wires embedded in the reservoir material or from a heating plate in the lid. This will further increase the efficiency of the reservoir's ability to humidify the air over the slides, as a pre-warmed reservoir will more easily humidify the space over the slides.

It should further be understood that the reservoir could be connected to external reservoirs by tubing or other means to allow increased capacity. Consequently the reservoir can be easily refilled. Also, different liquids can be added depending on the reaction and the protocol defining the sample processing.

It should be understood that, in some applications, the temperature might be ambient for long periods. That is, the slides may not be heated to above the ambient temperature. This is of relevance for storage of slides overnight before or after staining or for expanded incubations with reagents The reservoir can hold water, aqueous buffers, formamide, alcohols, dime dimethylsulfoxide. N-methyl-pyrolidone, non-aqueous buffers or complex mixtures containing inorganic salts, detergents, pH buffers, organic solvents, glycerol, oil and/or water as well as mixtures of the above-mentioned liquids.

Further, it should be understood that the composition of the liquid might include an anti microbial agent, an UV or other protective agents.

Further, it should be understood that the composition of the liquid in the reservoir might not be the same as in the vapor phase i.e. the vapor in the atmosphere in the environment between the reservoir material and the biological sample and reagents on a carrier. By adjusting the composition of the liquid in the reservoir, the composition of the vapors over the slides may be controlled. Specifically, through adjustment of the temperature of the liquid components in the reservoir, the content in the environmental vapor phase can be influenced. Experience has proven that, by maintaining a high humidity close to 100% during the relevant processing, the water content in the sample will, by the end of such processing (typically after a heating, and cooling and storing over night) be about the optimum for obtaining a perfect staining of the sample.

Further, it should be understood that the current invention especially relates to semi or fully automated instruments. Especially, computer controlled and programmable automated instruments for handling and processing slides will benefit from this invention.

The humidity above slides positioned individually, or in rack or carrousel arrangements in instruments can be controlled by the current invention. In fact, the invention is not limited to any particular arrangement of the slides on a slide platform. The reservoirs can be positioned in a stationary position adjacent to the slides.

Alternatively, the reservoirs or slides can be moved to be adjacent to each other when humidity is to be controlled. The reservoir can be single use, disposable or more permanently used in a semi or fully automated instrument, Of particular relevance is the use of a lid made entirely or partly of the reservoir of the invention. The lid may be placed adjacent to and preferably facing the slide, and the lid controls the humidity, i.e. a sufficiently wet lid will provide for almost 100% relative humidity. Preferably, the lid will be placed over the slide while the slide is positioned over a heating device. Reagents or other liquids can be added to the slide through one or several holes in the lid.

An automated dispensing device can deliver the reagents. Similarly, liquids can be added to the reservoir by automated dispensing devices in the instrument.

Further, it should be understood that the current invention would also function as a general warmer of microscope slides or other support's, by specifying a constant time and uniform temperature and humidity.

Another application, which will benefit from the current invention, is ISH on arrays. The arrays can contain thousands of spots or dots of sample. For example, the spots or dots could comprise immobilized tissue, genetic material, DNA, cDNA or RNA. The processing and visualization protocols resemble the protocols of more traditional ISH. Similarly, the control of humidity is essential for consistent results.

Applications using flat membranes or gels, like the one used in western and northern blots and treatment of electrophoresis gels will benefit from the highly controlled humidity and temperature of the current invention.

The PCR and LCR technique is only with difficulty performed in situ on samples mounted on slides. One of the problems is the lack of standardization with respect to temperature ramp time and uniform humidity control. The PCR or LCR procedures, which include repeated changes of temperature for long periods could benefit from the current invention.

Another application, which will benefit from the current invention, is the implementation of ISH on arrays. The arrays can contain thousands of spots, dots, sample dots or tissue samples on a single small or large slide or planar support. The uniformity of treatment over the many dots with respect to temperature and humidity is particularly important to ensure reproducible results.

Also, it should be understood that the current invention could reduce the humidity. The ability of the reservoir to efficiently adsorb moisture will create a dehumidifying system. As an example, such ability could be desirable when the temperature of the slide is decreased, which implies that some vapor in the air over the slide will be released as water, and this water has to be removed from the air over the slide. By having the hydrophilic reservoir, such vapor can be adsorbed on the hydrophilic fibers.

For example, by using a dry reservoir, with no or little liquid present, the high area surface removes the liquid between the space of the slides and the reservoir. This will result in fast dehydration of the slides. Furthermore, applying heat to the slides will increase the speed and efficiency of the dehydration process. For example, as described previously, the typical ISH protocol includes a dehydration step after the stringency wash step. The stringency wash is followed by two wash steps, by which the slides are immersed in a series of baths with increasing ethanol concentration and left to air-dry, before addition of mounting medium.

By using a reservoir with the capability to adsorb liquid, the number of steps in the process can be reduced. Heat applied to the slides will further speed up the process. In summary, an efficient dehumidifying system can reduce the steps and reagents needed for dehydration of slides.

The invention further relates to a method of processing biological samples wherein at least one biological sample is arranged on a carrier member, for treatment in order to prepare the sample by staining for a visual analysis of the sample, characterised by maintaining substantially at least 80% relative humidity above the sample through the close presence of a reservoir filled with water. Preferably, the method is characterized by maintaining relative humidity in the atmosphere above the sample of substantially at least 85% and, preferably, at least 90%, and, more preferably, at least 95% relative humidity and, most preferably, 99-100 relative humidity through the close presence of a reservoir, filled with water.

When carrying out the method of processing, it is preferred to supply the reservoir with water after the arrangement of the samples on the carrier members. If the lid with the reservoir material comprising the content of water is left open for a substantial time, the water may ooze downwards flowing out of the reservoir. Preferably, the lid is closed and positioned in its normal, horizontal position when it contains water—and during the processing of the samples.

Finally, the invention relates to the use of a reservoir in an apparatus for executing a method of processing biological samples, wherein at least one biological sample is arranged on a carrier member, for treatment in order to prepare the sample by staining. Experiences have indicated that the invention is particularly useful for hybridising a sample for performing an analysis in which DNA is the target, for HPV, Her-2, Top2A; for hybridising a sample for performing an analysis in which RNA is the target; for HPV; for performing IHC analysis; for p16. Her-family including phosphorylated ER/PR, MIB-1, and for hybridising a sample for performing an analysis from the group comprising ISH, HPV, HER 2, HER2 FISH, Topo II, telomers, EGRr, C-Myc, Epstein-Barr virus, Herpes simplex virus and Human cytomegalo virus, Chronic Myelogenous Leukemia (CML), acute myeloid leukemia (AML), Chromosome banding and paints.

BRIEF DESCRIPTION OF THE DRAWINGS

The object and features of the present invention can be more fully understood and better appreciated with reference to the attached drawings, which are schematic representations only and not necessarily drawn to scale, wherein.

DETAILED DESCRIPTION OF THE INVENTION

The present invention relates to an improved apparatus and methods for processing biological samples. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. Although various components are discussed in the context of a particular initial design, it should be understood that the various elements can be altered and even replaced or omitted to permit other designs and functionality as appropriate. Thus, the present invention is not intended to be limited to the embodiments shown but is to be accorded the widest scope consistent with the principles and features described, herein. To more particularly appreciate the features and advantages of preferred apparatuses and methods in accordance with the present invention, the reader is referred to the appended FIGS. 1-16 in conjunction with the following, discussion. It is to be understood that the drawings are diagrammatic and schematic representations only and are neither limiting of the scope of the present invention nor necessarily drawn to scale.

Figure 1:
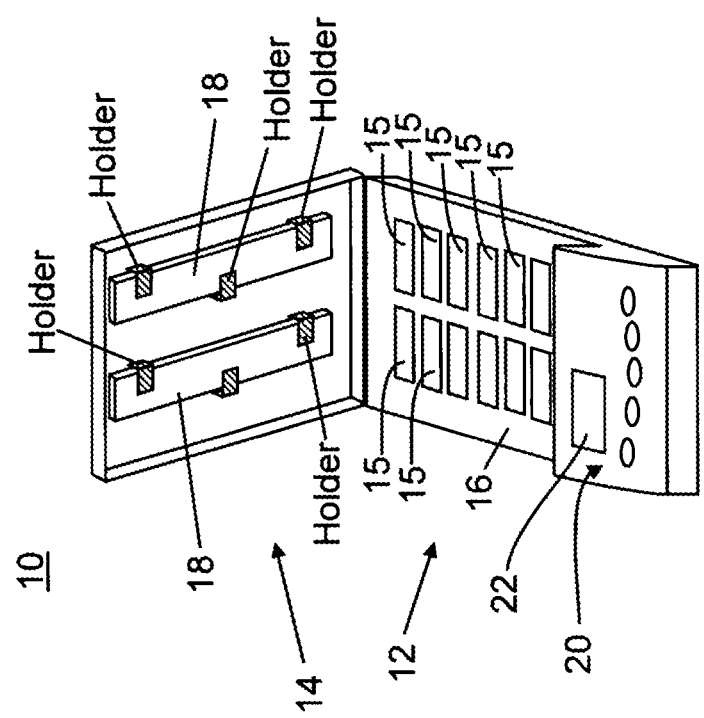
FIG. 1 shows a preferred embodiment of an apparatus in accordance with the present invention with the lid open.

FIG. 1 illustrates as an example an embodiment of an apparatus 10 according to the present invention. The apparatus comprises a bottom member 12 and a lid member 14. Preferably, the bottom member 12 and the lid member 14 are connected through a hinge, which is not shown. In the closed position illustrated in FIG. 2 the two members provide a closed or at least semi-closed chamber.

Figure 3:
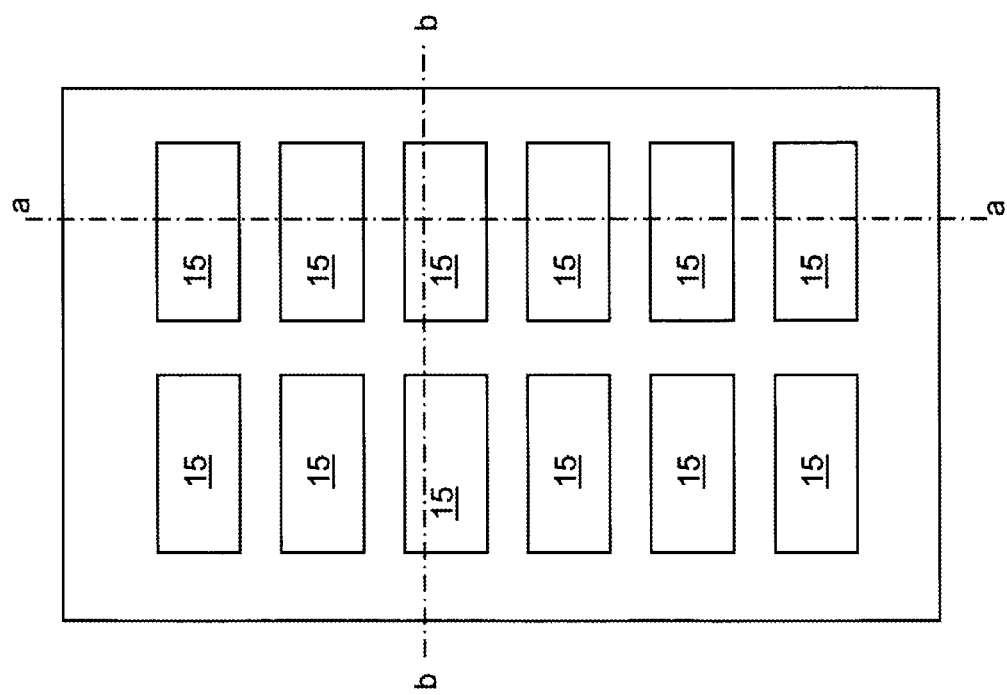
FIG. 3 shows a schematic view of an arrangement of carrier members on a bottom member of the apparatus of FIG. 1.
Figure 11:
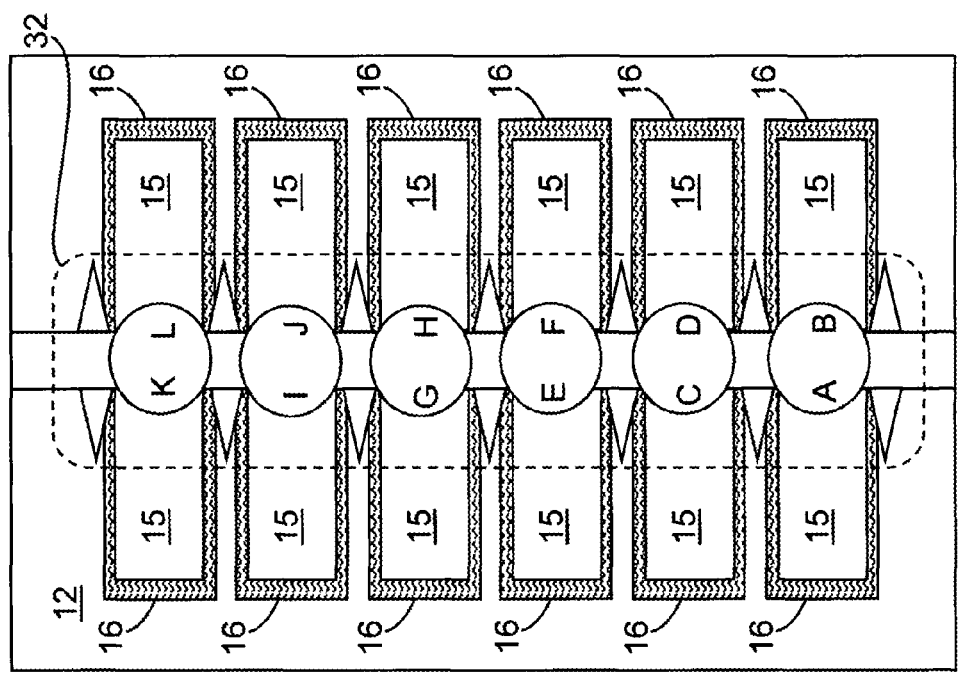
FIG. 11 shows a slide locator assisting the location of the slides on the bottom member of an apparatus as shown in FIG. 1, 2, 9, or 10.
Figure 12:
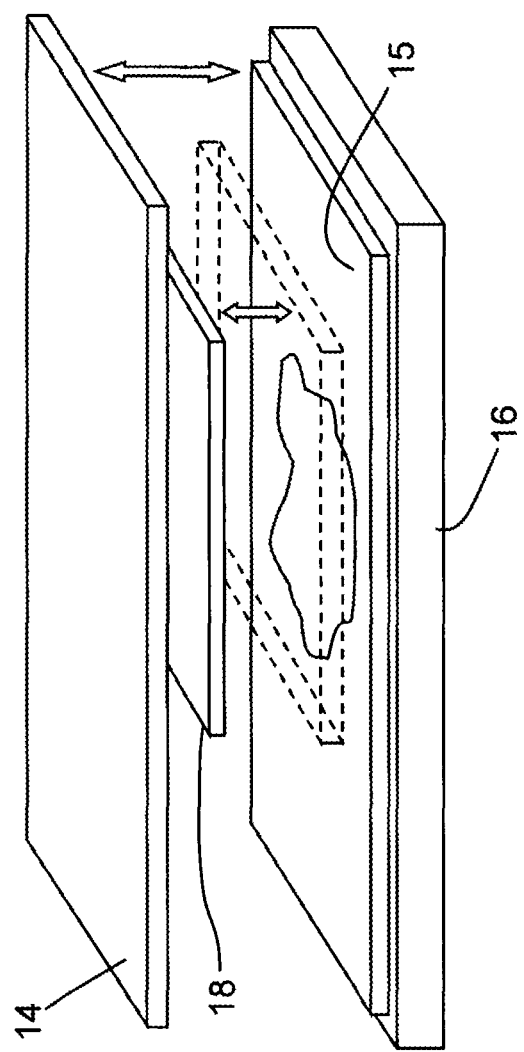
FIG. 12 shows a sample on a slide arranged on a heating plate and covered by a reservoir and a lid according to a method of the present invention.
Figure 13:
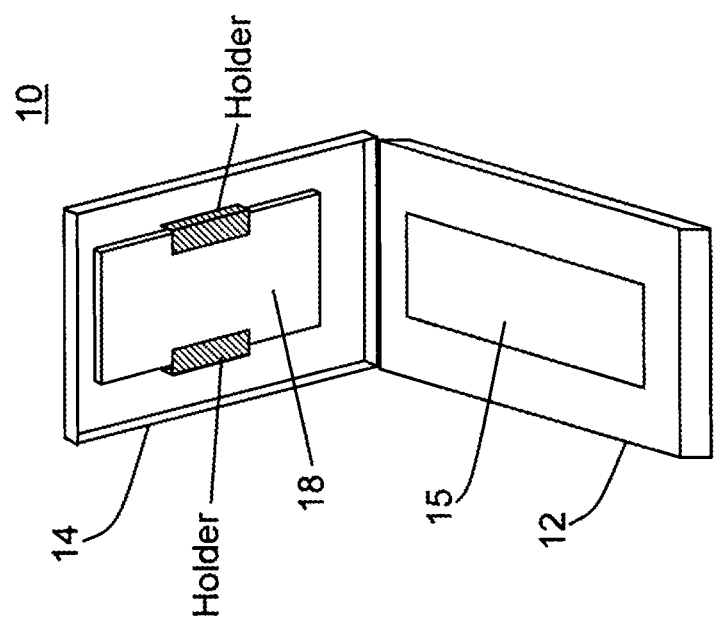
FIGS. 13 and 14 show an apparatus similar to the apparatus shown in FIGS. 9 and 10, but designed for only one slide.
Figure 14:
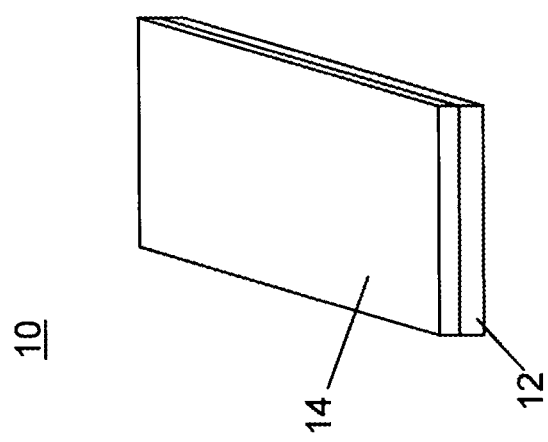
Figure 15:
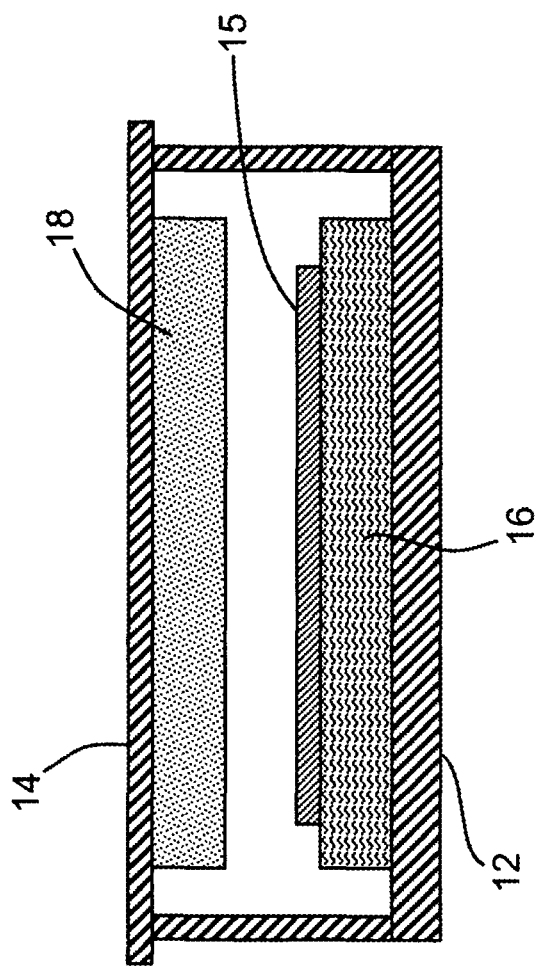
FIG. 15 shows a sectional view of the apparatus of FIGS. 13-14.

A plurality of biological samples on carrier members 15 may be arranged on the bottom member 12 e.g. as shown in FIGS. 3 and 11. Typically the samples may be tissue samples on microscope slides 15. An apparatus of this kind is manufactured and sold by StatSpin, Mass., US and by DakoCytomation, Denmark A/S.

Figure 4:
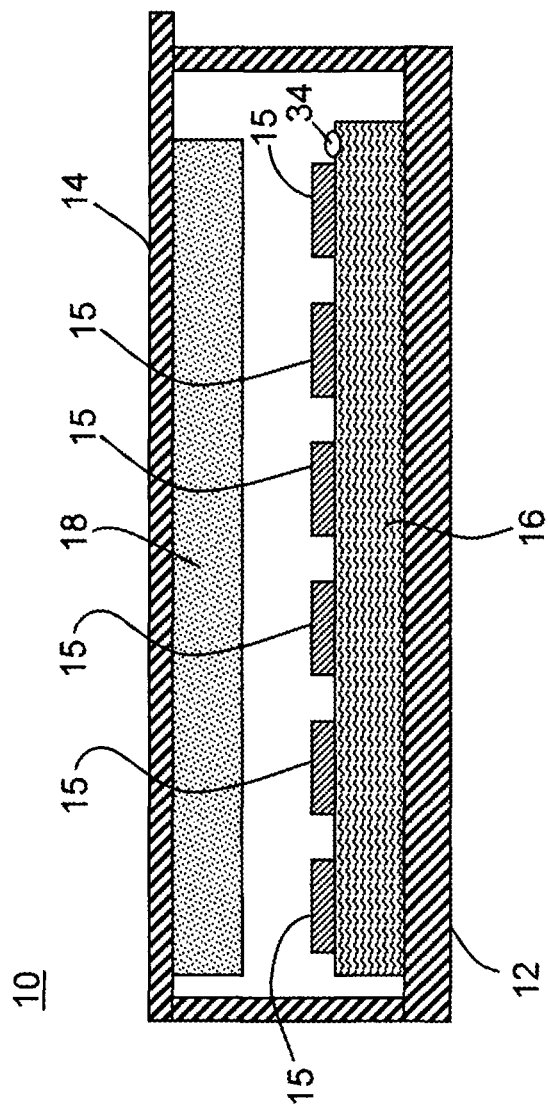
FIG. 4 shows a sectional view of the apparatus of FIG. 3 along the line a-a in FIG. 3.

The bottom member 12 includes a temperature controlled heating plate 16, as illustrated in FIG. 4. The heating plate 16 can be made from heat conducting material such as a metal, e.g. such as copper. Alternatively it could be a heat-conducting polymer. The heating plate includes heating means (not shown) such as beating wires for electrical heating, as well as sensor means 34 for sensing the temperature. Such temperature regulation is well known and will not be described in further details here. Preferably, also cooling means (e.g. Peltier elements and/or fan(s) blowing air), are provided in order to enable a ramped temperature profile. The final result of the sample treatment may be highly dependent on an exact optimised temperature profile, requiring that the temperature can be changed rapidly according to the requirements defined at a protocol for the treatment of the biological samples presently arranged in the apparatus.

Figure 2:
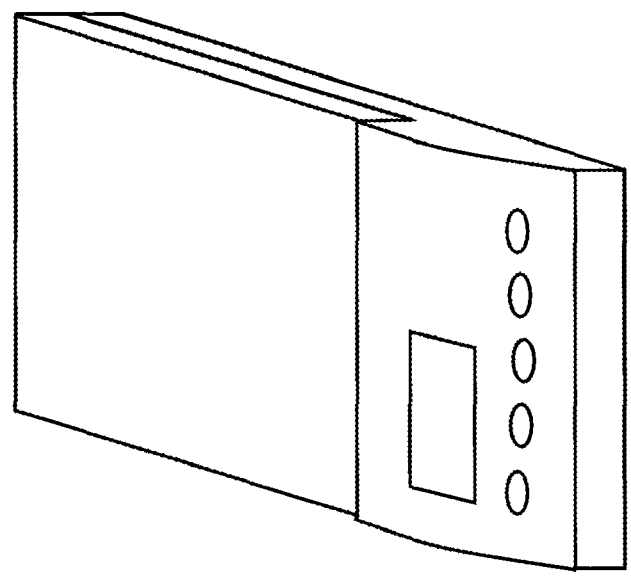
FIG. 2 shows the same apparatus as in FIG. 1 with the lid closed.

Preferably, the lid member 14 is provided with holding means, such as a grid, slots and/or fingers (not shown), supporting two humidity control strips 18 (FIGS. 4-6), arranged to be located above the biological samples when the lid 14 is closed, thereby covering the bottom member 12, as indicated in FIG. 2. The strips 18 act as water reservoirs ensuring a presence of water inside the closed apparatus during the treatment of the biological samples. The strips may be attached by any known kind of attachments or adhering means, or may be integrated into the lid or cover 14.

In a preferred embodiment, the lid member 14 may be provided with further heating and/or cooling means 16a (FIG. 5A), as well as temperature sensing means. Preferably, a temperature-controlling unit in the apparatus is arranged to allow for setting the temperature of the lid to a value different from the temperature selected fir the heating member 16 in the bottom member 12 in order to accelerate a release or absorption of vapor from the chamber. This could be specifically relevant during a rapid heating or cooling Phase of the sample processing during which the relative humidity can be difficult to control without this extra heating or cooling of the water reservoir.

In a further embodiment, the lid member 14 may be provided with a further reservoir 28 (FIG. 6) that allows refilling with liquid 28a during the sample processing.

It is essential that the strips IS have large internal surfaces compared to their external surfaces as well as to their total volume. The material may be of a kind comprising pores, forming the cavities accommodating the water. It is however presently preferred that the cavities are thrilled by spaces between randomly located bonded fibers, preferably having hydrophilic properties. The strips or reservoirs 18 can be made of a number of different materials, non-limiting examples include polymeric fiber composites and blends, glass fiber materials, expanded porous polymers, porous ceramics, Rockwool™, wood pulp, cardboard, leather or celluloses based materials.

Non-limiting, examples of materials for strips or reservoirs 18 include materials containing polyethylene, polypropylene, polyurethanes, polysulfones, polyvinyl, polyacrylic compositions, ethylene Vinyl Acetate, viscose rayon, polystyrene, macroreticular polystyrene, aliphatic, or phenol-formaldehyde condensate polymers, epoxy, cotton, polysaccharide, modified polysaccharides, wood pulp, calcium carbonate, silica gels, glass fiber, bentonite, perlite or zeolite. Other preferred materials include man-made or synthetic polymeric bonded, non-bonded, woven or knitted fibers, micro fibers, textiles or tufted textiles. More preferably the materials are made of bonded polyamide, polyester, polyolefins or cellulose acetate fibers.

In the presently preferred embodiment, the strips 18 are oblong plates made of non-woven and bonded blends of hydrophilic modified polypropylene and polyethylene micro fibers. Preferably, the material has a density from 0.050 to 1.5 gram/cm$^3$, more preferably from 0.075 to 0.75 gram/cm$^3$. This composition provides the strips with extremely large internal surfaces. The hydrophilic properties enable the internal surfaces to adhere to tiny little water drops, providing a very large surface of water versus air, thereby enabling and improving a fast exchange and balancing between the liquid phase and the vapor phase of the water.

Preferably, the macroscopic surface area of the strips (reservoir) 18 facing towards the carrier member with the sample is more than 10% of the total carrier member area, and preferably more than 30% of the total carrier member area even more preferably more than 50% of the total carrier member area, and, in the most preferred embodiment, more than 80% of the total carrier member area.

In a presently preferred embodiment, the strips 18 are about 2 mm thick, about 28 mm wide, and about 250 mm long. This structure provides a large surface of the strip facing the surface of the sample within a short distance from the sample. Preferably, the humidity control strip is located close to the sample in order to improve the fast exchange and supply of humid air. Preferably, the strips may hold more than 10 microliters in total per slide, more preferably more than 200 microliters in total per slide, and yet more preferably, more than 500 microliters in total per slide, and even more preferably, more than 1000 microliters in total per slide.

By mounting the control strips on the inner surface of the lid and preferably directly above the sample carriers the distance from the strips to the sample is minimized. Typically the distance may be 1 or 2 mm or even less, but always greater than zero so a layer of air and vapor separates the strip from the sample. The control strip should not get in touch with the sample.

In a further advantageous embodiment the strips may have a curved surface structure and uneven surfaces, such as a corrugated surface. Thereby the external surface comprising openings into the interior surfaces becomes large improving a rapid exchange of vapors, more specifically air and vapor of water providing almost 100% relative humidity.

In yet a further advantageous embodiment the humidity control strips 18 may have been impregnated with an anti microbial agent, an UV agent or other protective agents.

In the presently preferred embodiment the reservoir 28 is located above the sample on the carrier member so that the water supply is assisted through gravitation.

As explained earlier, a high humidity is essential to the final result of the staining of the biological samples. The presence of water is essential in order to maintain a high humidity. The treatment of the samples including several, possibly rapid temperature changes necessitates a rapid exchange between the liquid phase and the vapor phase of the water in order to ensure maintenance of a high relative humidity in the atmosphere above the samples. Such high relative humidity can be maintained through the use of the apparatus according to the invention incorporating the strips 18.

In the presently preferred embodiment, the strips are made of materials selected for their hydrophilic properties. However, other fluids might be contemplated, and in such cases the strip material must be chosen to co-operate with such fluid, e.g. a formamide. More specifically the type, shape and size of the reservoir material should be selected to optimise surface properties to match with the liquid surface tension.

Figure 7:
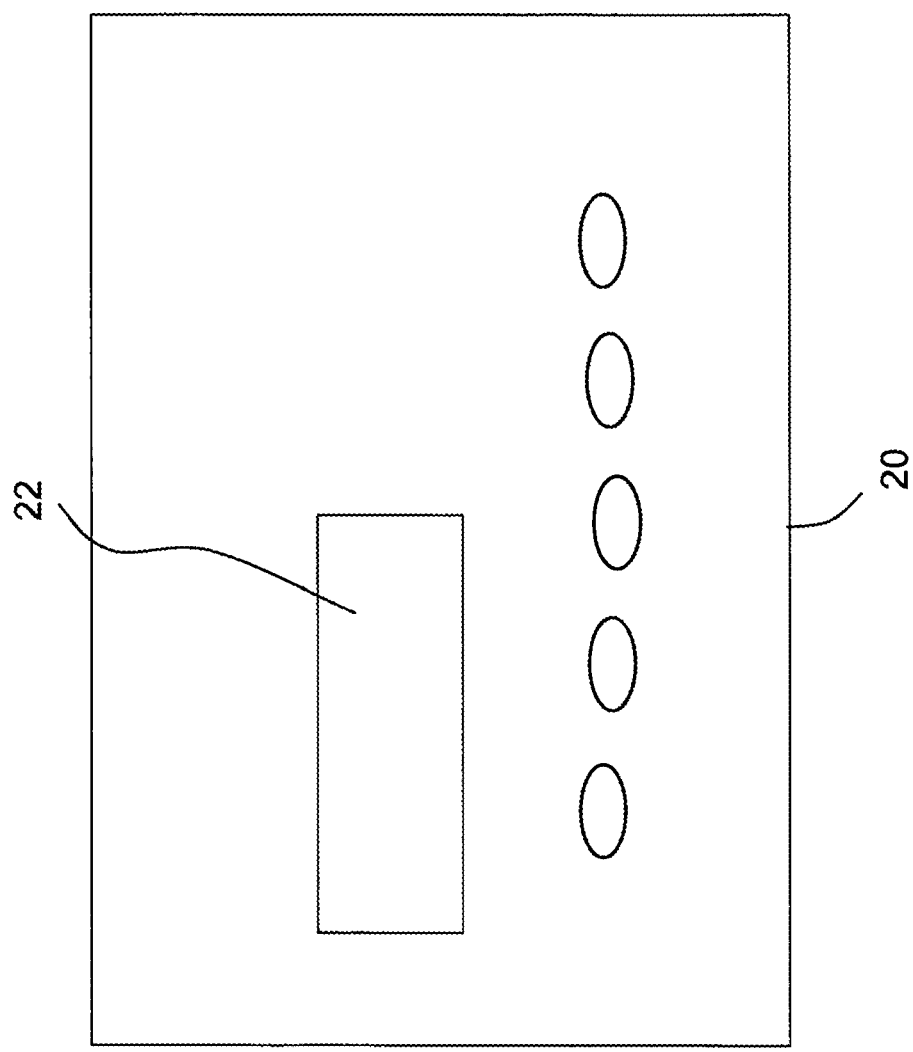
FIG. 7 shows the display and keypad of the apparatus of FIGS. 1 and 2.

In a preferred embodiment, the apparatus comprises data processing means as well a data input and output means 20, such as a keyboard or keypad and a display means 22 in FIGS. 1 and 7, or is adapted for communication with a computer, such as a PC. Preferably, the data processing, means may receive input from the temperature sensing means, and should be able to provide control signals to the heating and/or cooling means.

The computer may be provided with software and instructions enabling an automatic control of temperature and humidity inside the apparatus according to protocols specifying the conditions, e.g. temperatures and times, for the treatment of the samples.

In a further embodiment, the lid 14 itself is a sheet of hydrophilic material of a type or material as described previously herein for strips 18.

Heating wires may be embedded in the hydrophilic material. Also, the material may be bi-layered.

The lid 14 may simply be arranged on top of a heating plate carrying the sample carriers (microscope slides).

The following examples show preferred methods of how to use the preferred embodiment of an automatic apparatus:

Example A

Unit Power Up

After a user assures that the unit is plugged into an appropriate outlet, the user moves a power switch (not shown) to its "ON" position. The instrument then audibly beeps to announce that the power has been turned on, a cooling fan and heating not shown) will start and a Main Menu as Shown in Table I is displayed on display means 22, when the heating plate in the instrument has reached a delimit temperature of 37° C.

TABLE I

Run a PGM
Edit a PGM
Create a PGM

Example B

Denaturation and Hybridization Program

After the Main Menu screen is displayed, a cursor on the menu highlights the "Run a PGM" line of the menu. The user then presses an "Enter" key of the input and output means 20 to accept this menu item.

Subsequently, using the arrow keys, the user scrolls through various program numbers or program names. To accept the selection of a program, the user presses the "Enter" button or key of the input and output means 20. The display 22 then confirms the PGM number/name and Denaturation and Hybridization times and temperatures, an example of which is shown in Table II. The cursor highlights the "Run PGM" line. The user then presses the "Enter" button or key to accept this choice.

TABLE II

PGM 01 Her2
82° C.: 05; 45° C. 20:00
Run PGM
Main Menu

The display 22 then prompts the user to "Add Slides and Close Lid" as illustrated in Table III. Before adding slides, the user inserts two Humidity Control Strips 18 into the inside slide lid. After strip insertion, and after adding the slides, the user saturates the strips 18 with distilled water or equivalent (approx. 13 mL for dry strips). The cursor then highlights "Start" line. The user presses the "Enter" button or key to run the program.

TABLE III

PGM 01 Her2
Add Slides - Close Lid
Start
Main Menu

To return to the Main Menu, the user moves the cursor to highlight the "Main Menu" line of the display 22 and presses the "Enter" button or key. The display indicates "heating" and current temperature of the slides. Once the temperature reaches a denaturation set point, the denaturation time will count down from the set time as shown in Table IV.

TABLE IV

PGM 01 Her2
Denat in Process
Denat: 82° C. 02:28
Present Temp: 82° C.

The apparatus will then automatically cool to the hybridization set temperature once denaturation is completed (Table V).

TABLE V

Please Wait
Cooling to Hyb 45° C.
Present Temp: 58° C.

The hybridization time will then count down from the set, time once temperature reaches a hybridization set point.

Upon program completion, the unit will audibly beep to alert the user and the display will show "Process Complete" as shown in Table VI. The hybridization temperature will be maintained until an "End PGM/Main Menu" menu selection is accepted by pressing the "Enter" button of input and output means 20. Before pressing the "Enter" button, the user may remove slides for further processing. If the "End PGM/Main Menu" selection is not accepted within the first minute at program completion, the hybridization time will start counting the total time at hybridization temperature.

TABLE VI

PGM 01 Her2
PROCESS COMPLETE
Total Hyb Time 21:05
End PGM/Main Menu

Example C

Run a Hybridization Only Program

After the Main Menu screen is displayed, a cursor on the menu highlights the "Run a PGM" line of the menu. The user then presses an "Enter" key of the input and output means 20 to accept this menu item.

Subsequently, using arrow keys, the user scrolls through various program numbers or program names. To accept the selection of a program, the user presses the "Enter" button or key of the input and output means 20. The user selects a Hybridization Only program and the display 20 then confirms the PGM number/name and times and temperatures for a Hybridization Only protocol, examples of which are shown in Table VII. The cursor highlights the "Run PGM" line.

TABLE VII

PGM 02 EBV
Hyb: 55° C. 01:30
Run PGM
Main Menu

The user then installs two Humidity Control Strips 18 into the inside slide lid. After strip installation, and after adding the slides, the user saturates the strips 18 with distilled water or equivalent (approx. 13 mL for dry strips). The cursor highlights the "Start" line and the user then presses the "Enter" key or button to run the program as shown in Table VIII.

TABLE VIII

PGM 02 EBV
Add Slides - Close Lid
Start
Main Menu

The instrument will heat slides to the hybridization temperature as indicated in Table VIIIa.

TABLE VIIIa

Please Wait
Heating to Hyb 55° C.
Present Temp: 45° C.

Once hybridization temperature is reached the display changes as shown in table VIIIb and the time will count down from the set time.

TABLE VIIIb

PGM 02 EBV
Hyb in Process
Hyb 55° C. 01:30
Present Temp: 55° C.

Upon program completion, the unit audibly beeps to alert the user and the display 22 shows the message "Process Complete" Table IX). The Hybridization temperature will be maintained until the "End PGM/Main Menu" selection is accepted by pressing the "Enter" button. Before pressing the "Enter" button, the user may remove slides for further processing. If the "End PGM/Main Menu" selection is not accepted within the first minute of program completion, the hybridization time will start counting the total time at hybridization temperature.

TABLE IX

PGM 02 EBV
PROCESS COMPLETE
Total Hyb Time 02:15
End PGM/Main Menu

Example D

Fixed Temperature Program

After the Main Menu screen is displayed, a cursor on the menu highlights the "Run a PGM" line of the menu. The user then presses an "Enter" key of the input and output means 20 to accept this menu item.

Subsequently, using arrow keys, the user scrolls through various program numbers or program names. To accept the selection of a program, the user presses the "Enter" button or key of the input and output means 20. The user selects a Fixed Temperature program. The display 20 then confirms the PGM number/name and the Fixed Temperature (Table X) and the cursor highlights the "Run PGM" line of the display 22.

TABLE X

PGM 03 Appl
Fixed: 65° C.
Run PGM
Main Menu

By pressing the "Enter" button or key of input and output means 20 to run the program the instrument will heat to the fixed temperature as indicated in Table XI.

TABLE XI

Please Wait
Heating to Fxd: 65° C.
Present Temp: 30° C.

When the fixed temperature is reached, the display 22 then prompts the user to "Add Slides and Close Lid". Before adding slides, the user installs two Humidity Control Strips into the inside slide lid. After strip installation, and after adding the slides the user saturates the strips 18 with distilled water or equivalent (approx. 13 mL for dry strips) and closes the lid. The cursor highlights the "Start" line on display 22 (Table XII). The user then presses the "Enter" button of the input and output means 20 to continue the program.

TABLE XII

PGM 03 Appl
Add Slides - Close Lid
Start
Main Menu

To return to the Main Menu, the user moves the cursor to highlight the "Main Menu" line of display 22 and presses the "Enter" button of input and output means 20. The display 22 then indicates the present temperature of slides as shown in Table XIII and the tinier counts elapsed time. (Pressing the "Enter" button by the user will reset the timer to zero).

TABLE XIII

PGM 03 Appl
Fixed Temp: 65° C.
Reset Timer 01:18:10
End PGM/Main Menu

The user may use the Arrow keys of the input and output means 20 to move the highlighted display to the "End PGM/Main Menu" line and then press the "Enter" button to end the program.

As the above examples (Example A through Example D) indicate, the reservoirs 18 which are the humidity control strips may be useful in a hybridizer. However they can be used in many other apparatuses. FIG. 8 and FIGS. 12-16 show a single tissue slide 15 on a heating plate 16 covered by a reservoir 18 according to the present invention. Such arrangement may be incorporated in several types of apparatus for processing samples, such as automatic stainers, both of the carousel type and as well as stainers with robots moving reagents and or slides.

Figure 5:
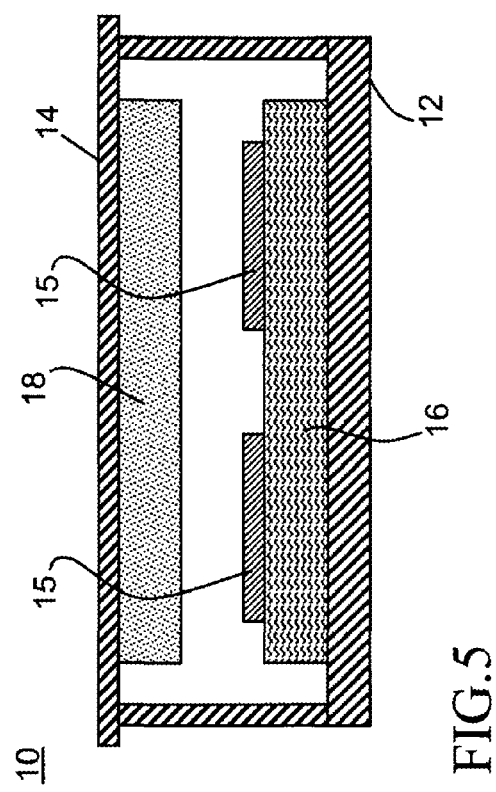
FIG. 5 shows a sectional view of the apparatus in FIG. 3 along the line b-b of FIG. 3.
Figure 5A:
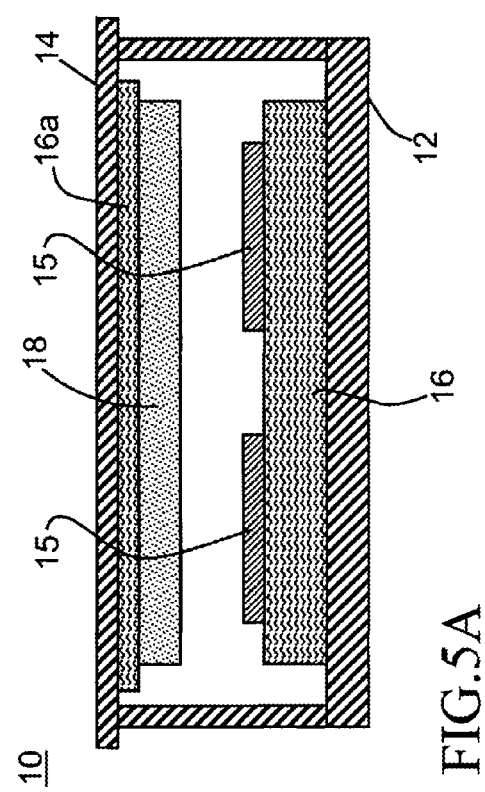
FIG. 5A shows a sectional view similar to FIG. 5, but with a heating plate in the lid.
Figure 6:
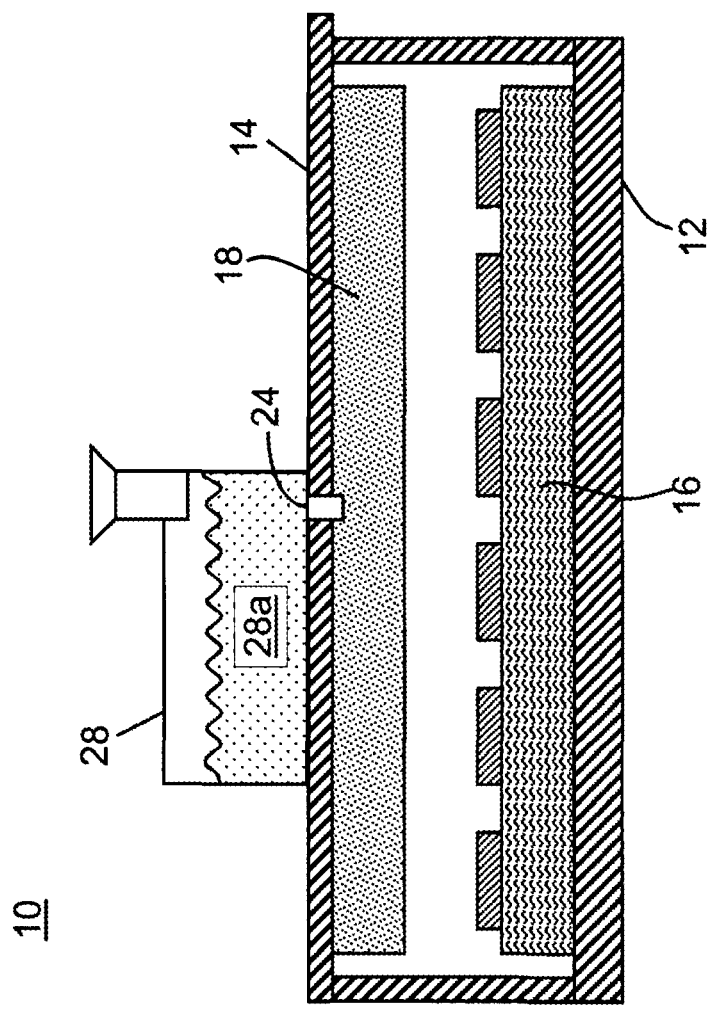
FIG. 6 shows a sectional view similar to FIG. 5 of an embodiment of an apparatus in accordance with the present invention having an external reservoir.
Figure 8:
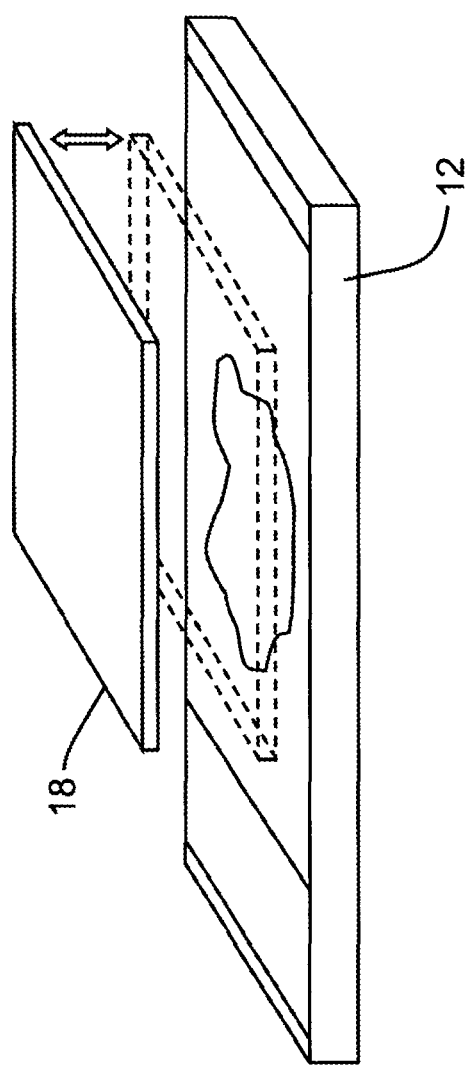
FIG. 8 shows a single tissue slide on a heating plate, covered by a reservoir according to an embodiment in accordance with the invention.

Also the arrangement shown in FIG. 8 and FIGS. 12-16 may be used in a tilted version. Also the reservoir 18 as shown in FIG. 8 may be incorporated into a lid 14 similar to the embodiment shown in FIG. 1, but with only one reservoir and one slide 15. A heating plate 16a may be attached or embedded in the lid 14, e.g. as shown in FIG. 5A.

Figure 16:
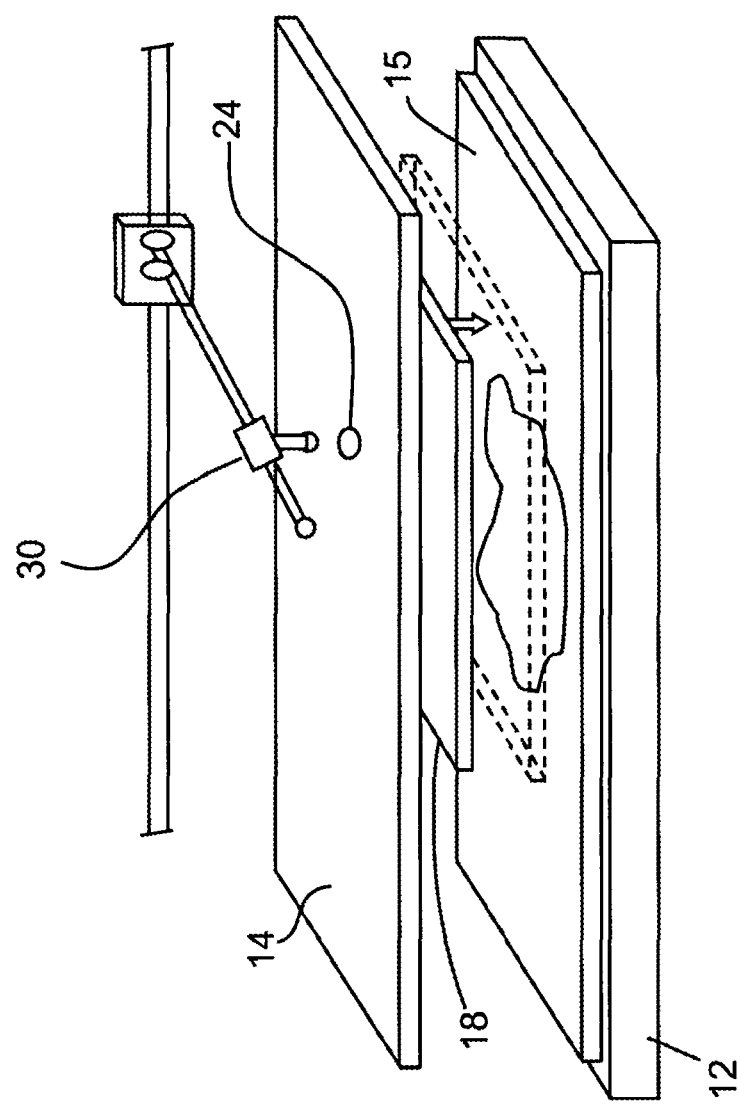
FIG. 16 shows an arrangement similar to FIGS. 12-14, including a robot arm.

In FIG. 16 a robot arm 30 is shown arranged above the lid 14. The lid 14 is provided with a hole 24 providing an inlet for fluid to the reservoir 18 and enabling the robot to provide a fluid, such as water or a reagent to the reservoir and/or to the sample. This is in order to emphasize that the apparatus according to the present invention may be part of an automatic sample-processing instrument for processing a plurality of biological samples.

Figure 9:
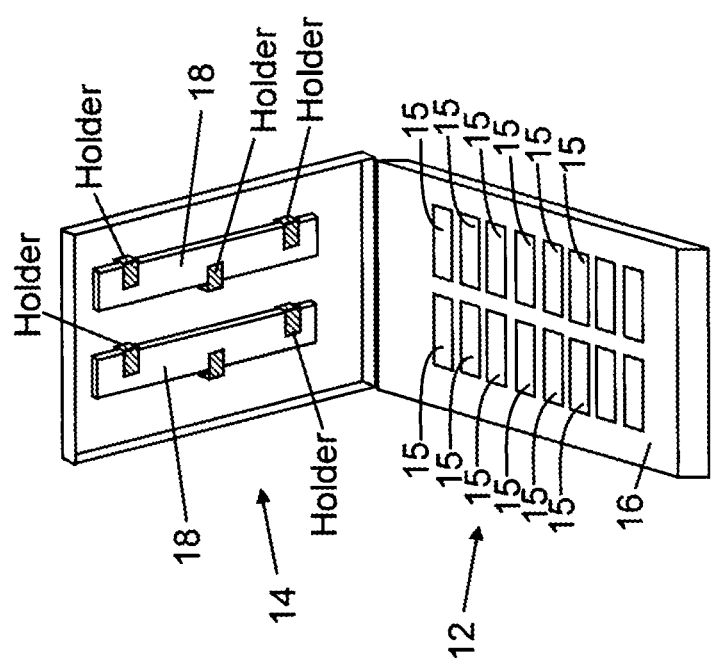
FIGS. 9 and 10 show a manual version of the apparatus of FIGS. 1 and 2.
Figure 10:
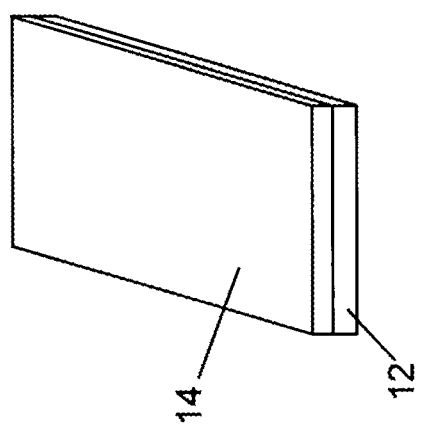

FIGS. 9 and 10 show a manual version of the apparatus, similar to the apparatus in FIGS. 1 and 2, but without computer assisted control.

FIG. 11 shows a view similar to FIG. 3, here with a slide locator 32 assisting the arrangement of 12 slides (A-L) on the bottom member of the apparatus in FIGS. 1 and 2.

The arrangements as shown in the drawings, and, specifically, the provision of a reservoir, in cooperation with the temperature sensors (not shown) and in cooperation with adequate control units, such as a computer, allow for a precise control of the climate around tissue on a slide 15. Specifically the hydrophilic adsorbent medium of the reservoir enables better staining results than hereto known when using automatic sample processing equipment.

In the following is presented seven examples taken from a validation test of the instrument.

In Example 1, the reservoir material was ordinary filter paper, not the recommended micro fiber material. In all other examples, the tests were carried out using the recommended micro fiber strips called "Hybridizer Humidity Control Strips". Dose strips were oblong plates made of non-woven and bonded blends of hydrophilic modified polypropylene and polyethylene micro fibers.

Example 1

FISH Validation

This is an example with TOP2A and paper filter strips. The on average acceptance criteria of TOP2A: Scoring 1.5-3 (signal intensity and specificity). A score of at least 2 on average or a deviation score within ±0.5 on average from reference is required. Individual outliers can be excluded due to obvious reasons and if these are reported. The first run with TOP2A on Hybridizer was performed with paper fitter strips (Filter strips), Table 1A. The instrument was tested with twelve slides from the same tissue block and resulted in an average score of the TOP2A signal intensities that resemble the signal intensities of the manual reference slides.

The signal intensities of Green signal, Centromer 17 on Hybridizer, score 2.0, did not resemble the intensities of the manual reference, score 3. Centromer signal intensities with a score less than 1.5 were observed for two of the twelve slides. The signal intensity of Centromer 17 was, however, on average 2, Red signal, HER2 did resemble the manual references, and therefore the acceptance criteria were barely fulfilled. The table shows Raw data of TOP2A probes on sections cut from the same formalin-fixed, paraffin embedded breast cancer tissue block; Performed on a hybridizer instrument with paper filter strips as humidity strips.

TABLE 1A

| Slide No. | Position in Hybridizer/Manual test | Signal Intensity Red | Signal Intensity Green | Tissue Structure |
|---|---|---|---|---|
| | | Run No. 1 | | |
| 1 | 1 | 2.5 | 2.5 | 3 |
| 2 | 2 | 2.5 | 2.5 | 3 |
| 3 | 3 | 1.5 | 1 | 3 |
| 4 | 4 | 3 | 2.5 | 3 |
| 5 | 5 | 3 | 2.5 | 3 |
| 6 | 6 | 2.5 | 2 | 3 |
| 7 | 7 | 2.5 | 3 | 3 |
| 8 | 8 | 2.5 | 1.5 | 2.5 |
| 9 | 9 | 2 | 1.5 | 2.5 |
| 10 | 10 | 3 | 2.5 | 3 |
| 11 | 11 | 2 | 1 | 2.5 |
| 12 | 12 | 2 | 2 | 3 |
| 13 | Manual test | 2.5 | 3 | 2.5 |
| 14 | Manual test | 2 | 3 | 2.5 |
| 1-12 | Mean | 2.4 | 2.0 | 2.9 |
| | Std | 0.469 | 0.656 | 0.226 |
| 13-14 | Mean | 2.3 | 3.0 | 2.5 |

Example 2

Example with TOP2A and DakoCytomation Hybridizer Humidity Control Strips

A run performed on the validation instrument No. 102 confirmed that the acceptance criteria were easily fulfilled if Hybridizer Humidity Control Strips (0.198 g/cm3) were used instead of paper filter strips.

The instrument test run was as good as the manual procedure,

In conclusion, the Hybridizer passed the acceptance criteria for TOP2A. The scores of the slides were, when Hybridizer Humidity Control Strips were used, as good as the manual procedures.

The table (Table 1B) shows Raw data of TOP2A probes on sections cut from the same formalin-fixed, paraffin embedded breast cancer tissue block, performed on hybridizer instrument with Hybridizer Humidity Control Strips (3 mm thick, 0.198 g/cm$^3$). Green signal, Centromer 17; Red signal, HER2.

TABLE 1B

| Slide No. | Position in Hybridizer/Manual test | Signal Intensity Red | Signal Intensity Green | Tissue Structure |
|---|---|---|---|---|
| | | Run No. 1 | | |
| 1 | 1 | 3 | 2.5 | 3 |
| 2 | 2 | 3 | 2.5 | 3 |
| 3 | 3 | 3 | 3 | 3 |
| 4 | 4 | 3 | 3 | 2.5 |
| 5 | 5 | 3 | 2.5 | 2.5 |
| 6 | 6 | 3 | 3 | 2.5 |
| 7 | 7 | 3 | 3 | 3 |
| 8 | 8 | 3 | 3 | 3 |
| 9 | 9 | 3 | 2.5 | 3 |
| 10 | 10 | 3 | 3 | 3 |
| 11 | 11 | 3 | 3 | 2.5 |
| 12 | 12 | 3 | 3 | 3 |
| 13 | Manual test | 3 | 3 | 3 |
| 1,4 | Manual test | 3 | 3 | 3 |
| 1.5 | Manual test | 3 | 2.5 | 3 |
| 1-12 | Mean | 3.0 | 2.8 | 2.8 |
| | Stdv | 0.000 | 0.246 | 0.246 |
| 13-15 | Mean | 3.000 | 2.833 | 3.000 |
| | Stdv | 0.0 | 0.3 | 0.0 |

Example 3

HER2

The on average acceptance criteria of HER2: Scoring 1.5-3 (signal intensity and specificity). A score of at least 2 on average or a deviation score within 0.5 on average from reference is required. Individual outliers can be excluded due to obvious reasons and if these are reported. The run with HER2 on Hybridizer was performed with Hybridizer Humidity Control Strips (0.270 g/cm3). The instrument was tested with tissue sections of different thickness (2 μm to 6 μm) from the same formalin-fixed paraffin-embedded tissue block. The run resulted in scores of signal intensities and tissue structures that resembled the manual reference. No score deviation of ±0.5 grade or above on average was observed. In conclusion, the Hybridizer passed the acceptance criteria for HER2. The scores of the slides were as good as the manual procedures. Table 2 shows raw data of the HER2 Probe; performed on hybridizer instrument with Hybridizer Humidity Control Strips (2 mm thick, 0.270 g/cm$^3$). Green signal, Centromer 17; Red signal, HER2.

TABLE 2

| Slide No. | Thickness of Tissue | Position in Hybridizer/Manual test | Run No. 1 Signal Intensity Red | Signal Intensity Green | Tissue structure |
|---|---|---|---|---|---|
| 1 | 2 μm | 1 | 3 | 3 | 2.5 |
| 2 | | 2 | 3 | 2.5 | 2.5 |
| 3 | | 3 | 3 | 3 | 2 |
| 4 | | Manual test | 3 | 3 | 2.5 |
| 5 | | Manual test | 3 | 3 | 2.5 |
| 6 | 4 μm | 4 | 3 | 2.5 | 2.5 |
| 7 | | 5 | 2.5 | 2.5 | 2.5 |
| 8 | | 6 | 2.5 | 2.5 | 2.5 |
| 9 | | Manual test | 2 | 2.5 | 2.5 |
| 10 | | Manual test | 2.5 | 3 | 2.5 |
| 11 | 6 μm | 7 | 3 | 3 | 3 |
| 12 | | 8 | 2.5 | 2 | 3 |
| 13 | | 9 | 3 | 3 | 3 |
| 14 | | Manual test | 2.5 | 3 | 2.5 |
| 15 | | Manual test | 2.5 | 3 | 3 |
| 1, 2, 3 | 2 μm | Mean | 3.0 | 2.8 | 2.3 |
| 6, 7, 8 | 4 μm | Mean | 2.7 | 2.5 | 2.5 |
| 11, 12, 13 | 6 μm | Mean | 2.8 | 2.7 | 3.0 |
| Manual 4, 5 | 2 μm | Mean | 3.0 | 3.0 | 2.5 |
| Manual 9, 10 | 4 μm | Mean | 2.3 | 2.8 | 2.5 |
| Manual 14, 15 | 6 μm | Mean | 2.5 | 3.0 | 2.8 |

Example 4

MLL and ETV6

The on average acceptance criteria of MLL and ETV6: Scoring 1.5-3 (signal intensity and specificity). Score deviation of ±0.5 on average from reference is allowed. Individual outliers can be excluded due to obvious reasons and if these are reported.

The run on Hybridizer was performed with Hybridizer Humidity Control Strips (0.270 g/cm$^3$). The instrument was tested with sample specimens from the same lot of metaphase spreads. The run resulted in better scores of the MLL and ETV6 signal intensities than observed with the manual references. The structure of the cells resembled the manual references. In conclusion, the Hybridizer passed the acceptance criteria for MLL and ETV6. The scores of the slides were better than the manual procedures. The scores obtained on Hybridizer were, though, for both probes more than 0.5 grade higher in signal than the manual references. These scores are above the deviations described in the acceptance criteria, but still acceptable.

Table 3 shows raw data of translocation probes. MLL and ETV6, on metaphase spreads, performed on hybridizer instrument No. 25 with Hybridizer Humidity Control Strips (2 mm thick, 0.270 g/cm$^3$).

TABLE 3

| Slide No. | Probe mix | Position in Hybridizer | Run in Hybridizer No. 25 Signal in interphases | Signal in metaphases | Structure of inter- and metaphases | Comments |
|---|---|---|---|---|---|---|
| 1 | ETV6 | 4 | 3 | 3 | 2 | — |
| 2 | | 8 | 3 | 3 | 2 | — |
| 3 | | 3 | 2.5 | 2.5 | 2 | — |
| 4 | | Manual test | 2 | 2 | 2 | — |
| 5 | | | 2 | 2 | 2 | — |
| 6 | MLL | 5 | 2.5 | 3 | 2 | — |
| 7 | | 6 | 2.5 | 2.5 | 2 | — |
| 8 | | 1 | 2.5 | 2.5 | 2.5 | — |
| 9 | | Manual test | 1 | 2 | 2.5 | — |
| 10 | | | 2 | 2 | 2 | — |

| Method | Signal of inter- and metaphases | Structure |
|---|---|---|
| Hybridizer 1-3 | 2.83 ± 0.26 | 2 ± 0 |
| Hybridizer 6-8 | 2.58 ± 0.20 | 2.2 ± 0.29 |
| Manual 4-5 | 2.0 ± 0 | 2 |
| Manual 9-10 | 1.75 ± 0.5 | 2.25 |

Example 5

This example relates to CISH validation of HPV on Formalin-fixed paraffin-embedded tissue blocks. The on average acceptance criteria of HPV on cells: 2.5-4 signal; negative control; 0-1 background; ±0.25 grade divergence from manual staining (for individual slides).

The run with HPV probes on Hybridizer was performed with Hybridizer Humidity Control Strips. The signal intensities fully resembled those of the manual references. No score deviation was observed. The background levels appeared to be lower with Hybridizer than with the manual method.

In conclusion, the scores of signal intensities of the slides were as good as the manual procedure, when the hybridisation was performed with the humidity control strips Table 4 Raw Data of HPV Probe on Tissue.

The test ran on a Hybridizer with Hybridizer Humidity Control Strips.

TABLE 4

| Method | Slide number | Block No. | Signal | Background |
|---|---|---|---|---|
| Hybridizer | 1 | 236 | 3 | 0.25 |
| Hybridizer | 2 | 340 | 3 | 0.25-0.5 |
| Hybridizer | 6 | 340 | 3 | 0.25 |
| Hybridizer | 7 | 236 | 3 | 0.5 |
| Hybridizer | 11 | 236 | 3 | 0.5 |

TABLE 4-continued

| Hybridizer | 12 | 340 | 3 | 0.75 |
|---|---|---|---|---|
| Manual | 13 | 236 | 3 | 0.25 |
| Manual | 14 | 236 | 3 | 1 |
| Manual | 15 | 340 | 3 | 0.75 |
| Manual | 16 | 340 | 3 | 0.5 |

| Method | Signal | Background |
|---|---|---|
| Hybridizer Slide 1, 2, 6, 7, 11, 12 | 3 ± 0 | 0.42-0.46 ± 0.19-0.20 |
| Manual Slide 13-16 | 3 ± 0 | 0.63 ± 0.32 |

Example 6

Telomere

The on average acceptance criteria of Telomere: Scoring 1.5-3 (signal intensity and specificity). Score deviation of ±0.5 on average from reference is allowed. Individual outliers can be excluded due to obvious reasons and if these are reported.

The run on Hybridizer was performed with Hybridizer Humidity Control Strips (0.22-25 g/cm$^3$). The validation instrument was tested with sample specimens from two different lots of metaphase spreads. The run resulted in scores of signal intensities and tissue structures that resembled the manual reference for both FISH (K 5325) and Cy3 (K 5326) labelled Telomere probes. No score deviation above ±0.5 grade on average was observed. The structure of the cells resembled the manual references.

In conclusion, the Hybridizer passed the acceptance criteria for Telomere. The scores of the slides were as good as the manual procedures.

Table 5: Raw Data of Telomere Probes, on Two Different Metaphase Spreads.

Performed on hybridizer instrument with Hybridizer Humidity Control Strips (0.22-0.25 g/cm$^3$).

TABLE 5

| Slide No. | Metaphase preparation | Probe | Position in Hybridizer | Signal intensity | Background | Average signal intensity | Average signal background |
|---|---|---|---|---|---|---|---|
| 1 | 080903- | Telomere/ | 1 | 3 | 0 | 3 ± 0 | 0 ± 0 |
| 2 | MEM | FITC | 2 | 3 | 0 | | |
| 3 | | | 3 | 3 | 0 | | |
| 4 | | | Manual | 3 | 0 | 3 | 0 |
| 5 | | | test | 3 | 0 | | |
| 6 | 221203- | | 4 | 3 | 0.5 | 2.67 ± 0.29 | 0.5 ± 0 |
| 7 | MEM | | 5 | 2.5 | 0.5 | | |
| 8 | | | 6 | 2.5 | 0.5 | | |
| 9 | | | Manual | 3 | 0 | | 0 |
| 10 | | | test | 3 | 0 | | |
| 11 | 080903- | Telomere/ | 7 | 3 | 0 | 3 ± 0 | 0 ± 0 |
| 12 | MEM | Cy3 | 8 | 3 | 0 | | |
| 13 | | | 9 | 3 | 0 | | |
| 14 | | | Manual | 3 | 0 | 3 | 0 |
| 15 | | | test | 3 | 0 | | |
| 16 | 221203- | | 10 | 3 | 0 | 3 ± 0 | 0 ± 0 |
| 17 | MEM | | 11 | 3 | 0 | | |
| 18 | | | 12 | 3 | 0 | | |
| 19 | | | Manual | 3 | 0 | 3 | 0 |
| 20 | | | test | 3 | 0 | | |

Example 7

EBER (EBV)

The on average acceptance criteria of EBER: Scoring 1.5-3 (signal intensity and specificity). Score deviation of ±0.5 on average from reference is allowed. Individual outliers can be excluded due to obvious reasons and if these are reported.

The run on Hybridizer was performed with Hybridizer Humidity Control Strips (0.22-25 g/cm3). The run resulted in scores of signal intensities that resembled the manual reference. No score deviation of ±0.5 grade or above on average was observed. The background appeared to be lower with Hybridizer than with the manual method.

In conclusion, the Hybridizer passed the acceptance criteria for EBER. The scores of the slides were as good as the manual procedures.

Table 6: Raw Data of EBER Probes on Two EBV-Positive Tissue.

Performed on Hybridizer instrument with Hybridizer Humidity Control Strips (0.22-0.25 g/cm$^3$).

TABLE 6

| Slide No. | Tissue | Position in Hybridizer | Probe mix | Signal intensity | Background |
|---|---|---|---|---|---|
| 1A | A | 1 | EBER Y5200 | 2 | 0 |
| 1B | | | Neg. control | 0 | 0 |
| 2A | | 2 | EBER Y5200 | 2.5 | 0.5 |
| 2B | | | Neg. control | 0 | 0 |
| 3A | B | 3 | EBER Y5200 | 2 | 0.5 |
| 3B | | | Neg. control | 0 | 0 |
| 4A | | 4 | EBER Y5200 | 2 | 0 |
| 4B | | | Neg. control | 0 | 0 |
| 5A | A | Manual test | EBER Y5200 | 2.5 | 0.5 |
| 5B | | | Neg. control | 0 | 0 |
| 6A | | | EBER Y5200 | 2.5 | 1 |
| 6B | | | Neg. control | 0 | 0.5 |
| 7A | B | | EBER Y5200 | 2.5 | 0.1 |
| 7B | | | Neg. control | 0 | 0.5 |
| 8A | | | EBER Y5200 | 2 | 0 |
| 8B | | | Neg. control | 0 | 0.5 |

| Method | Signal intensity | Background |
|---|---|---|
| Hybridizer EBER 1A-4A | 2.13 ± 0.25 | 0.25 ± 0.28 |
| Hybridizer neg. control 1B-4B | 0 ± 0 | 0 ± 0 |
| Manual EBER 5A-8A | 2.38 ± 0.25 | 0.4 ± 0.45 |
| Manual neg. control 5B-8B | 0 ± 0 | 0.38 ± 0.25 |

LIST OF REFERENCE NUMBERS

The following is a list of reference numbers used in the accompanying drawings and referred to in this specification: 10—apparatus, Hybridizer; 12—bottom member; 14—lid member; 15—carrier members, which may be microscope slides; 16—temperature-controlled heating plate; 16a—heating plate in lid 14; 18—humidity control strips or reservoir; 20—data input and output means including a display and key pad; 22 display; 24 hole; 28 further reservoir for refilling the reservoir 18; 28a—liquid within reservoir 28; 30—robot arm; 32—slide sorter.

An improved apparatus and methods for processing biological samples and a reservoir therefore have been disclosed. Although the present invention has been described in accordance with the embodiments shown and discussed, one of ordinary skill in the art will readily recognize that there could be variations to the embodiments and those variations would be within the spirit and scope of the present invention. For instance, although the preferred embodiment of the present invention is described in the context of a Hybridizer for 12 slides, it will be appreciated that the teachings of the present invention are applicable to any number of slides that are processed in any number of chambers equipped with any system for controlling temperature and humidity, e.g., in automated sample processing equipment comprising a plurality of heater plates, each of them being arranged to carry a single microscope slide with tissue. Also, even though all figures show the reservoir above the slide on the heater plate in the bottom part, it must be understood that the chamber might be turned upside down so that the reservoir would be arranged below the slide. Accordingly, many modifications may be made by one of ordinary skill in the an without departing from the spirit and scope of the invention, which is defined by the appended claims.

The invention claimed is:

1. An automatic stainer for staining biological samples, said stainer comprising:
a carrier member supported within a chamber of the stainer, the carrier member configured to receive a biological sample and a reagent for staining the biological sample;
a bottom member supporting said at least one carrier member;
a hydrophilic porous solid reservoir configured to sorb and desorb water and water vapor;
a lid for the chamber, detachable from the bottom member, the lid and the bottom member forming a closed chamber when the lid is positioned atop the bottom member, wherein the lid is configured to position the reservoir inside the closed chamber directly above the at least one biological sample such that the reservoir does not touch said at least one biological sample, when said lid is positioned atop the bottom member to form the closed chamber; and
a sample temperature controlling device below said at least one carrier member controlling the temperature of said at least one carrier member and said at least one biological sample, wherein said reservoir either sorbs or desorbs water and water vapor so as to control relative humidity within said chamber at above 85% relative humidity, when said lid is positioned atop the bottom member to form the closed chamber.

2. The stainer of claim 1, wherein the stainer is carousel type.

3. The stainer of claim 1, wherein the stainer is robotic and configured to move reagents and slides.

4. The stainer of claim 1, wherein said lid may be removed from the bottom member to access said at least one biological sample and said reservoir.

5. The stainer of claim 1, wherein said reservoir is less than 5 cm from said at least one carrier member.

6. The stainer of claim 1, wherein said reservoir is less than 1.0 cm from said at least one carrier member.

7. The stainer of claim 1, wherein said reservoir is less than 0.5 cm from said at least one carrier member.

8. The stainer of claim 1, wherein said sample temperature controlling device further comprises at least one element selected from the group consisting of a temperature sensor, heating wires, an inductive heater, and a cooling device for cooling the at least one biological sample.

9. The stainer of claim 1, wherein relative humidity in the closed chamber is controlled by desorption of water and water vapor from said reservoir during heating of said at least one biological sample or absorption of water and water vapor from said closed chamber during cooling of said at least one biological sample.

10. The stainer of claim 1, wherein said reservoir is shaped as a flat sheet.

11. The stainer of claim 10, wherein a thickness of said reservoir is less than 10% of a length of said reservoir.

12. The stainer of claim 1, wherein said water further comprises at least one additive, the at least one additive selected from the group consisting of an anti-microbial agent, an inorganic salt, a detergent and an organic solvent.

13. The stainer of claim 1, wherein said reservoir is made of a material from the group consisting of polymeric fiber composites, polymeric fiber blends, glass fiber materials, expanded porous polymers, porous ceramics, wood pulp, cardboard, leather and cellulose-based materials, or is made of a material comprising a composition chosen from the group consisting of polyethylene, polypropylene, polyurethanes, polysulfones, polyvinyl, polyacrylics, ethylene Vinyl Acetate, viscose rayon, polystyrene, macroreticular polystyrene, aliphatic polymers, phenol-formaldehyde condensate polymers, epoxy, cotton, polysaccharide, modified polysaccharides, wood pulp, calcium carbonate, silica gels, glass fiber, bentonite, perlite and zeolite.

14. The stainer of claim 1, wherein said reservoir is made of a material comprising bundles of fibers or loose material chosen from the group consisting of polymeric bonded fibers, non-bonded fibers, woven fibers, knitted fibers, micro fibers, textiles, tufted textiles, bonded polyamide fibers, polyester fibers, polyolefin fibers, cellulose acetate fibers, and non-woven and bonded blends of hydrophilic modified polypropylene and polyethylene micro fibers, wherein the bundles of fibers or loose material are retained by a thin wall of film.

15. The stainer of claim 1, wherein the type, shape and size of material of which said reservoir is comprised is selected to optimize surface properties of said material with regard to a surface tension of said water.

16. The stainer of claim 1, wherein material of which said reservoir is comprised has a density from 0.050 to 1.5 gram/cm3.

17. The stainer claim 1, wherein said reservoir has the ability to hold at least a predefined minimum volume of liquid per carrier member, the predefined minimum volume being chosen from the group consisting of 10 micro-liters, 100 micro-liters, 200 micro-liters, 500 micro-liters, and 1000 microliters.

18. The stainer of claim 1, further comprising a second reservoir outside the closed chamber.

19. A method of staining biological samples using an automatic stainer, the method comprising:
   supporting a biological sample on a carrier member;
   dispensing a reagent on the carrier member to stain the biological sample;
   providing a bottom member for supporting said carrier member;
   positioning a lid, detachable from the bottom member, above the carrier member to form a closed chamber with the bottom member, wherein positioning the lid above the carrier member also positions a hydrophilic porous solid reservoir configured to sorb and desorb water and water vapor directly above the at least one biological sample such that the reservoir does not touch said at least one biological sample;
   controlling the temperature of said carrier member and said at least one biological sample with a sample temperature controlling device positioned below said carrier member;
   and maintaining at least 85% relative humidity inside the chamber through the sorption or desorption of water and water vapor.

20. An apparatus adapted for nucleic acid denaturization and hybridization of at least one biological sample on at least one carrier member in a chamber, said apparatus comprising:
   a computer configured for data processing and control signal communication;
   a bottom member supporting said at least one carrier member;
   a hydrophilic porous solid reservoir configured to sorb and desorb water and water vapor;
   a lid for the chamber, detachable from the bottom member, the lid and the bottom member forming a closed chamber when the lid is positioned atop the bottom member, wherein the lid is configured to position the reservoir inside the closed chamber directly above the at least one biological sample such that the reservoir does not touch said at least one biological sample, when said lid is positioned atop the bottom member to form the closed chamber; and
   a sample temperature controlling device below said at least one carrier member controlling the temperature of said at least one carrier member and said at least one biological sample, wherein said reservoir either sorbs or desorbs water and water vapor so as to control relative humidity within said chamber at above 85% relative humidity, when said lid is positioned atop the bottom member to form the closed chamber.

21. The apparatus of claim 20, wherein the computer is configured to received data input from a keyboard or keypad and output data on a display.

22. The apparatus of claim 20, wherein the computer is configured to communicate with the sample temperature controlling device and provide heating and cooling control signals.

* * * * *